US008105825B2

(12) United States Patent
Dhadialla et al.

(10) Patent No.: US 8,105,825 B2
(45) Date of Patent: Jan. 31, 2012

(54) MULTIPLE INDUCIBLE GENE REGULATION SYSTEM

(75) Inventors: Tarlochan Singh Dhadialla, Indianapolis, IN (US); Dean Ervin Cress, Souderton, PA (US); Glenn Richard Carlson, North Wales, PA (US); Robert Eugene Hormann, Melrose Park, PA (US); Subba Reddy Palli, Lansdale, PA (US); Arthur John Kudla, Charlottesville, VA (US); Ronald Phillip Herzig, Jr., Barboursville, VA (US); Mohan Philip, Charlottesville, VA (US)

(73) Assignee: Intrexon Corporation, Blacksburg, VA (US)

( * ) Notice: Subject to any disclaimer, the term of this patent is extended or adjusted under 35 U.S.C. 154(b) by 663 days.

(21) Appl. No.: 09/965,697

(22) Filed: Sep. 27, 2001

(65) Prior Publication Data

US 2002/0110861 A1  Aug. 15, 2002

Related U.S. Application Data

(60) Provisional application No. 60/237,446, filed on Oct. 3, 2000.

(51) Int. Cl.
  *C12N 5/00* (2006.01)
  *C12N 15/00* (2006.01)
  *C12N 5/07* (2010.01)
  *C12N 5/10* (2006.01)
  *C12N 5/071* (2010.01)
  *C12N 5/02* (2006.01)
  *C12N 1/00* (2006.01)
  *C12P 21/06* (2006.01)
  *C07H 21/04* (2006.01)
  *C07K 1/00* (2006.01)

(52) U.S. Cl. ............ 435/325; 435/320.1; 435/352; 435/354; 435/366; 435/410; 435/252.1; 435/254.1; 435/254.2; 435/69.1; 536/23.4; 536/23.5; 530/350

(58) Field of Classification Search .................. None
See application file for complete search history.

(56) References Cited

U.S. PATENT DOCUMENTS

| | | | |
|---|---|---|---|
| 4,631,211 A | 12/1986 | Houghten | |
| 4,859,609 A | 8/1989 | Dull et al. | |
| 4,954,655 A | 9/1990 | Kelly | |
| 4,981,784 A | 1/1991 | Evans et al. | |
| 4,985,461 A | 1/1991 | Hsu et al. | |
| 5,010,175 A | 4/1991 | Rutter et al. | |
| 5,071,773 A | 12/1991 | Evans et al. | |
| 5,117,057 A | 5/1992 | Hsu et al. | |
| 5,171,671 A | 12/1992 | Evans et al. | |
| 5,225,443 A | 7/1993 | Murphy et al. | |
| 5,283,173 A | 2/1994 | Fields et al. | |
| 5,378,726 A | 1/1995 | Yanagi et al. | |
| 5,424,333 A | 6/1995 | Wing | |
| 5,429,952 A | 7/1995 | Garner et al. | |
| 5,459,127 A | 10/1995 | Felgner et al. | |
| 5,514,578 A | 5/1996 | Hogness et al. | |
| 5,530,021 A | 6/1996 | Yanagi et al. | |
| 5,530,028 A | 6/1996 | Lidert et al. | |
| 5,599,904 A | 2/1997 | Evans et al. | |
| 5,639,616 A | 6/1997 | Liao et al. | |
| 5,641,652 A | 6/1997 | Oro et al. | |
| 5,668,175 A | 9/1997 | Evans et al. | |
| 5,688,691 A | 11/1997 | Oro et al. | |
| 5,710,004 A | 1/1998 | Evans et al. | |
| 5,723,329 A | 3/1998 | Mangelsdorf et al. | |
| 5,880,333 A | 3/1999 | Goff et al. | |
| 5,919,667 A | 7/1999 | Gage et al. | |
| 5,939,442 A | 8/1999 | Evans et al. | |
| 5,989,863 A | 11/1999 | Tang et al. | |
| 6,013,836 A | 1/2000 | Hsu et al. | |
| 6,025,483 A | 2/2000 | Yanofsky | |
| 6,096,787 A | 8/2000 | Evans et al. | |
| 6,117,639 A | 9/2000 | Germann et al. | |
| 6,147,282 A | 11/2000 | Goff et al. | |
| 6,245,531 B1 | 6/2001 | Hogness et al. | |
| 6,258,603 B1 | 7/2001 | Carlson et al. | |
| 6,265,173 B1 | 7/2001 | Evans et al. | |
| 6,281,330 B1 | 8/2001 | Evans et al. | |
| 6,300,488 B1 | 10/2001 | Gage et al. | |
| 6,326,166 B1 | 12/2001 | Pomerantz et al. | |
| 6,333,318 B1 | 12/2001 | Evans et al. | |
| 6,379,945 B1 | 4/2002 | Jepson I et al. | |
| 6,410,245 B1 | 6/2002 | Northrop et al. | |
| 6,458,926 B1 | 10/2002 | Evans et al. | |
| 6,504,082 B1 | 1/2003 | Albertsen et al. | |
| 6,635,429 B1 | 10/2003 | Leid et al. | |
| 6,723,531 B2 | 4/2004 | Evans et al. | |
| 6,756,491 B2 | 6/2004 | Evans et al. | |

(Continued)

FOREIGN PATENT DOCUMENTS

CN 1245638 A1 3/2000

(Continued)

OTHER PUBLICATIONS

Fussenegger-M, Biotechnol. Prog. 17(1-51)2001.*
Moradopour-D et al. Biol Chem 379(1189-1191)1998.*
Hofmann-A et al., PNAS 93(5185-5190)1996.*
Lafont R. et al., Journal of Insect Science, 3(7)1-30, 2003.*
Wang et al. Nuc. Acids Res. 27: 4609-4618, 1999.*
Kaufman et al Blood 94: 3178-3184, 1999.*
Phillips, A., J Pharm Pharmacology 53: 1169-1174, 2001.*
Kufe et al (ed) Cancer Medicine BC Decker Inc. 2003, pp. 1-8, downloaded Dec. 3, 2008.*
Moradpour Darius et al., "Independent regulation of two separate gene activities in a continuous human cell line," *Biological Chemistry* Aug. 1998, 379, 1189-1191.

(Continued)

*Primary Examiner* — Shulamith H Shafer
(74) *Attorney, Agent, or Firm* — Sterne, Kessler, Goldstein & Fox P.L.L.C.

(57) ABSTRACT

The present invention relates to the field of biotechnology or genetic engineering. More specifically, the present invention relates to a multiple inducible gene regulation system that functions within cells to simultaneously control the quantitative expression of multiple genes.

31 Claims, 2 Drawing Sheets

U.S. PATENT DOCUMENTS

| | | | |
|---|---|---|---|
| 6,875,569 B2 | 4/2005 | Gage et al. |
| 6,939,711 B2 | 9/2005 | Goff et al. |
| 7,038,022 B1 | 5/2006 | Evans et al. |
| 7,045,315 B2 | 5/2006 | Evans et al. |
| 7,057,015 B1 | 6/2006 | Gage et al. |
| 7,091,038 B2 | 8/2006 | Palli et al. |
| 7,119,077 B1 | 10/2006 | Evans et al. |
| 7,183,061 B2 | 2/2007 | Jepson et al. |
| 7,456,315 B2 | 11/2008 | Hormann et al. |
| 7,531,326 B2 | 5/2009 | Kapitskaya et al. |
| 7,776,587 B2 | 8/2010 | Palli et al. |
| 7,807,417 B2 | 10/2010 | Palli et al. |
| 7,935,510 B2 | 5/2011 | Palli et al. |
| 2002/0110861 A1 | 8/2002 | Dhadialla et al. |
| 2002/0119521 A1 | 8/2002 | Palli et al. |
| 2004/0033600 A1 | 2/2004 | Palli et al. |
| 2004/0096942 A1 | 5/2004 | Kapitskaya et al. |
| 2004/0197861 A1 | 10/2004 | Palli et al. |
| 2004/0235097 A1 | 11/2004 | Zhang et al. |
| 2005/0266457 A1 | 12/2005 | Palli et al. |
| 2006/0100416 A1 | 5/2006 | Palli et al. |
| 2007/0161086 A1 | 7/2007 | Palli et al. |
| 2007/0300313 A1 | 12/2007 | Palli et al. |
| 2008/0064097 A1 | 3/2008 | Palli et al. |
| 2008/0115237 A1 | 5/2008 | Palli et al. |
| 2008/0145935 A1 | 6/2008 | Palli et al. |
| 2008/0176280 A1 | 7/2008 | Kapitskaya et al. |
| 2008/0216184 A1 | 9/2008 | Palli et al. |
| 2008/0235816 A1 | 9/2008 | Dhadialla et al. |
| 2008/0263687 A1 | 10/2008 | Kapitskaya et al. |
| 2008/0301825 A1 | 12/2008 | Palli et al. |
| 2011/0059525 A1 | 3/2011 | Palli et al. |
| 2011/0059530 A1 | 3/2011 | Palli et al. |

FOREIGN PATENT DOCUMENTS

| | | |
|---|---|---|
| CN | 1313276 C | 9/2001 |
| EP | 234944 A1 | 9/1987 |
| EP | 461809 B1 | 12/1994 |
| EP | 798378 A2 | 3/1997 |
| EP | 984 009 A1 | 3/2000 |
| EP | 984009 A1 | 3/2000 |
| EP | 1266015 B1 | 3/2001 |
| EP | 965644 B1 | 11/2007 |
| JP | 4178380 A | 6/1992 |
| WO | 8912690 A1 | 12/1989 |
| WO | 9200252 A1 | 1/1992 |
| WO | 9428028 A1 | 12/1994 |
| WO | 9637609 A1 | 5/1996 |
| WO | WO 96/27673 A1 | 9/1996 |
| WO | WO9627673 | 9/1996 |
| WO | 9735985 A1 | 3/1997 |
| WO | 9738117 A1 | 10/1997 |
| WO | 9833162 A2 | 1/1998 |
| WO | 9910510 A2 | 8/1998 |
| WO | 9910510 A3 | 8/1998 |
| WO | WO 98/35550 A2 | 8/1998 |
| WO | 9927365 A1 | 11/1998 |
| WO | WO 99/02683 A1 | 1/1999 |
| WO | WO9902683 | 1/1999 |
| WO | 9951777 A2 | 4/1999 |
| WO | 9951777 A3 | 4/1999 |
| WO | WO 99/26966 A2 | 6/1999 |
| WO | 9936520 A1 | 7/1999 |
| WO | 9958155 A1 | 11/1999 |
| WO | 0071743 A1 | 11/2000 |
| WO | WO 01/02436 A1 | 1/2001 |
| WO | 0136447 A2 | 5/2001 |
| WO | 0162780 A1 | 8/2001 |
| WO | WO 01/70816 A2 | 9/2001 |
| WO | WO0170816 | 9/2001 |
| WO | 0229075 A2 | 4/2002 |
| WO | 02066612 A2 | 8/2002 |
| WO | 02066613 A2 | 8/2002 |
| WO | 02066614 A2 | 8/2002 |
| WO | 02066615 A2 | 8/2002 |
| WO | 03105849 A1 | 6/2003 |
| WO | 2004005478 A2 | 1/2004 |
| WO | 2004072254 A2 | 1/2004 |
| WO | 2004078924 A2 | 9/2004 |
| WO | 2005017126 A2 | 2/2005 |
| WO | 2005108617 A2 | 11/2005 |
| WO | 2006083253 A1 | 8/2006 |
| WO | 9936520 A1 | 1/2008 |

OTHER PUBLICATIONS

Martinez A et al., "Creation of ecdysone receptor chimeras in plants for controlled regulation of gene expression," *Molecular and General Genetics*, Apr. 1999, 261, 546-552.

Kothapalli R et al., "Cloning and developmental expression of the ecdysone receptor gene from the spruce budworm, *Choristoneura Fumiferana*," *Developmental Genetics*, 1995, 17, 319-330.

Belshaw, P. et al., "Controlling protein association and subcellular localization with a synthetic ligand that induces heterodimerization of proteins," *Proc Natl Acad Sci U S A*, May 1996, 93, 4604-4607.

Chang, C. et al., "Evolution of a cytokine using DNA family shuffling," *Nat Biotechnol*, Aug. 1999, 17(8), 793-797.

Michnick, S. et al., "'Itching' for new strategies in protein engineering," *Nat Biotechnol*, Dec. 1999 17(12), 1159-1160.

No, D. et al., "Ecdysone-inducible gene expression in mammalian cells and transgenic mice," *Proc Natl. Acad. Sci USA*, Apr. 1996, 93, 3346-3351.

Ostermeier, M. et al., "A combinatorial approach to hybrid enzymes independent of DNA homology," *Nat Biotechnol*, Dec. 1999, 17(12), 1205-1209.

Stemmer, W. P. C., "DNA shuffling by random fragmentation and reassembly: In vitro recombination for molecular evolution," *Proc Natl Acad Sci USA*, Oct. 1994, 91(22), 10747-10751.

Sambrook, J., Fritsch, E. F. and Maniatis, T. *Molecular Cloning: A Laboratory Manual*, Second Edition, Cold Spring Harbor Laboratory Press, Cold Spring Harbor, 1989, particularly Chapter 11 and Table 11.1.

Ablordeppey et al., Is a Nitrogen Atom and Important Pharmacophoric Element in Sigma Ligand Binding? Bioorganic & Medicinal Chemistry (2000), 8(8), 2105-2111.

Nassif-Makki et al. Bisquatemary Ligands of the Common Allosteric Site of M2 Acetylcholine Receptors: Search for the Minimum Essential Distances between the Pharmacophoric Elements. Journal of Medicinal Chemistry (1999), 42(5), 849-858.

Malaska et al. Chemical modification of ring C of himbacine: discovery of a Pharmacophoric Element for M2-selectivity. Bioorganic & Medicinal Chemistry Letters (1995), 5(1), 61-6.

Kozikowski et al. Delineating the Pharmacophoric Elements of huperzine A: importance of the unsaturated three-carbon bridge to its AChE inhibitory activity. Journal of Medicinal Chemistry (1991), 34(12), 3399-402.

Belshaw et al. Rational design of orthogonal receptor-ligand combinations. Angewandte Chemie, International Edition in English (1995), 34(19), 2129-32.

Pierce et al. Computational binding studies of orthogonal cyclosporin-cyclophilin pairs. Angewandte Chemie, International Edition in English (1997), 36(13/14), 1466-1469.

Peet et al. Engineering Novel Specificities for Ligand-Activated Transcription in th enucelar Hormone Receptor RXR. Chemistry & Biology, 1998, 5, 1, 13-21.

Holt et al. Functional Expression of Exogenous Proteins in Mammalian Sensory Hair Cells Infected with Adenoviral Vectors. J Neurophysiol. (1999), 81(4), 1881-8.

Doyle et al. Journal of the American Chemical Society (2001), 123(46), 11367-11371.

Hoppe et al. Molecular Therapy (2000) 1(2), 159-164.

Ashburner M et al., "Temporal Control of Puffing Activity in Polytene Chromosomes", Cold Spring Harbor Symp. Quant. Biol., 1974, 38:655-662.

Dhadialla TS et al., "New Insecticides with Ecdysteroidal and Juvenile Hormone Activity", Annu. Rev. Entomol, 1998, 43:545-569.

Koelle MR et al., "The Drosophila EcR Gene Encodes an Ecdysone Receptor, a New Member of the Steroid Receptor Superfamily", Cell, 1991, 67:59-77.

Carlson GR et al. "The chemical and biological properties of methoxyfenozide, a new insecticidal ecdysteroid agonist." Pest Manag Sci. Feb. 2001;57(2):115-9.

Mouillet J.-F. et al., "Cloning of two putative ecdysteroid receptor isoforms from Tenebrio molitor and their developmental expression in the epidermis during metamorphosis", Eur. J. Biochem., 1997, 248:856-863.

Fujiwara H et el., "Cloning of an Ecdysone Receptor Homolog from Manduca sexta and the Developmental Profile of Its mRNA in Wings", Insect Biochem. Mol. Biol., 1995, 25: 845-856.

Martinez A et al., "Transcriptional activation of the cloned Heliothis virescens (Lepidoptera) ecdysone receptor (HvEcR) by MuristeroneA", Insect Biochem Mol Biol, 1999, 29:915-930.

Imhof MO et al., "Cloning of a Chironomous tentans cDNA Encoding a Protein (cEcRH) Homologous to the Drosphila melanogaster Ecdysteroid Receptor (dEcR)", Insect Biochem. Mol. Biol., 1993, 23:115-124.

Swevers L et al., "The Silkmoth Homolog of the Drosophila Ecdysone Receptor (B1 Isoform): Cloning and Analysis of Expression During Follicular Cell Differentiation", Insect Biochem. Mol. Biol., 1995, 25:857-866.

Cho W.-L. et al., "Mosquito Ecdysteroid Receptor: Analysis of the cDNA and Expression During Vitellogenesis", Insect Biochem. Mol. Biol., 1995, 25:19-27.

Hannan GN et al., "Cloning and Characterization of LcEcR: A Functional Ecdysone Receptor from the Sheep Blowfly *Lucilia cuprina*", Insect Biochem. Mol. Biol., 1997, 27:479-488.

Verras M et al., "Cloning and characterization of CcEcR: An ecdysone receptor homolog from the Mediterranean fruit fly *Ceratitis capitate*", Eur. J. Biocehm., 1999, 265:798-808.

Saleh DS et al., "Cloning and characterization of an ecdysone receptor cDNA from *Locusta migratoris*", Molecular and Cellular Endocrinology, 1998, 143:91-99.

Chung Arthur C.-K. et al., "Cloning of curstacean ecdysteroid receptor and retinoid-X receptor gene homologs and elevation of retinoid-X receptor mRNA by retinoic acid", Molecular and Cellular Endocrinology, 1998, 139:209-227.

Guo X et al., "Isolation of a Functional Ecdysteroid Receptor Homologue from the Ixodid Tick *Amblyomma americanum* (L.)", Insect Biochem. Mol. Biol., 1997, 27:945-962.

Evans RM, "The Steroid and Thyroid Hormone Receptor Superfamily", Science, 1988, 240:889-895.

Riddiford LM et al., "Ecdysone Receptors and Their Biological Actions", Vitamins and Hormones, 2000, 60:1-73.

Christopherson KS et al., "Ecdysteroid-dependent regulation of genes in mammalian cells by a Drosophila ecdysone receptor and chimeric transactivators", Proc. Natl. Acad. Sci. U.S.A., 1992, 89:6314-6318.

No D et al., "Ecdysone-inducible gene expression in mammalian cells and transgenic mice", Proc. Natl. Acad. Sci., 1996, 93:3346-3351.

Suhr ST et al., "High level transactivation by a modified Bombyx ecdysone receptor in mammalian cells without exogenous retinoid X receptor", Proc. Natl. Acad. Sci. U.S.A.,1998, 95:7999-8004.

Heberlein U et. al., "Characterization of Drosophila Transcription Factors That Activate the Tandem promoters of the Alcohol Dehydrogenase Gene", Cell, 1985, 41:965-977.

Wilson JM et al., "Hepatocyte-directed Gene Transfer in Vivo Leads to Transient Improvement of Hypercholesterolemia in Low Density Lipoprotein Receptor-deficient Rabbits", J. Biol. Chem., 1992, 267:963-967.

Neuberger MS et al., "Recombinant antibodies possessing novel effector functions", Nature, 1984, 312:604-608.

Antoniewski C et al., "The Ecdysone Response Enhancer of the Fbp1 Gene of Drosophila melanogaster Is a Direct Target for the EcR/USP Nuclear Receptor", Molecular and Cellular Biology, 1994, 14:4465-4474.

Morrison DA et al., "Isolation of Transformation-Deficient *Streptococcus pneumoniae* Mutants Defective in Control of competence, Using Isertion-Duplication Mutagenesis with the Erythromycin Resistance Determinant of pAMbeta1", J. Bacteriol, 1984, 159:870-876.

Metzger D et al., "The human oestrogen receptor functions in yeast", Nature, 1988, 334:31-36.

Godowski PJ et al., "Signal Transduction and Transcriptional Regulation by Glucocorticoid Receptor-LexA Fusion Proteins", Science, 1988, 241:812-816.

D'Avino PP et al., "The moulting hormone ecdysone is able to recognize target elements composed of direct repeats", Molecular and Cellular Endocrinology, 1995, 113:1-9.

Cherbas L et al., "Identification of ecdysone response elements by analysis of the Drosophila Elp28/29 gene", Genes & Development, 1991, 5:120-131.

Egea PF et al. "Effects of ligand binding on the association properties and conformation in solution of retinoic acid receptors RXR and RAR." J. Mol. Biol., 2001, 307(557-576).

Bonneton F et al. "Rapid divergence of the ecdysone receptor in Diptera and Lepidoptera suggests coevolution between ECR and USP-RXR." Mol Biol Evol. Apr. 2003;20(4):541-53.

Hayward DC et al. "The structure of the USP/RXR of Xenos pecki indicates that Strepsiptera are not closely related to Diptera." Dev Genes Evol. Apr. 2005;215(4):213-9.

Filmus J et al."Synergistic induction of promoters containing metal- and glucocorticoid-responsive elements."Nucleic Acids Res. Jun. 11, 1992; 20(11): 2755-2760.

Fields S et al. "A novel genetic system to detect protein-protein interactions." Nature 1989, 340:245-246.

Kakizawa T et al. "Ligand-dependent heterodimerization of thyroid hormone receptor and retinoid X receptor." J Biol Chem. Sep. 19, 1997;272(38):23799-804.

Leid M et al. "Purification, cloning, and RXR identity of the HeLa cell factor with which RAR or TR heterodimerizes to bind target sequences efficiently." Cell. Jan. 24, 1992;68(2):377-95.

Leonhardt SA et al. "Agonist and antagonists induce homodimerization and mixed ligand heterodimerization of human progesterone receptors in vivo by a mammalian two-hybrid assay." Mol Endocrinol. Dec. 1998;12(12):1914-30.

Licitra EJ et al. "A three-hybrid system for detecting small ligand-protein receptor interactions." Proc Natl Acad Sci U S A. Nov. 12, 1996;93(23):12817-21.

Perera SC et al "Studies on two ecdysone receptor isoforms of the spruce budworm, *Choristoneura fumiferana*."Mol Cell Endocrinol. Jun. 25, 1999;152(1-2):73-84.

Perera SC "An analysis of ecdysone receptor domains required for heterodimerization with ultraspiracle." Archives of Insect Biochem Physiol. 1999. 41:61-70.

Yao TP et al. "Drosophila ultraspiracle modulates ecdysone receptor function via heterodimer formation." Cell. Oct. 2, 1992;71(1):63-72.

Yao TP et al. "Functional ecdysone receptor is the product of EcR and Ultraspiracle genes." Nature. Dec. 2, 1993;366 (6454):476-9.

Cao S et al. "N'-tert-Butyl-N'-aroyl-N-(alkoxycarbonylmethyl)-N-aroylhydrazines, a novel nonsteroidal ecdysone agonist: syntheses, insecticidal activity, conformational, and crystal structure analysis." Canadian Journal of Chemistry, Mar. 2001 , 79(3):272-278.

Glass CK et al. "Nuclear Receptor Coactivators." Curr Opin Cell Biol. 1997, 9:222-232.

Egea PF et al. "Molecular recognition of agonist ligands by RXRs." Mol Endocrinol. 2002 16(5):987-97.

Brennan JD "Preparation and Entrapment of Fluorescently Labeled Proteins for the Development of Reagentless Optical Biosensors." Journal of Fluorescence, Dec. 1999, 9(4)295-312.

Wipf P et al. "Combinatorial synthesis and biological evaluation of library of small-molecule Ser/Thr-protein phosphatase inhibitors." Bioorg Med Chem. 1997, 5(1):165-77.

Andianov VG et al. "4-Amino-A2-1,2,4-ozadiazolines." Chemistry of Heterocyclic Compounds 1991, 22(2):216-218.

Andianov VG et al. "4-Aminofurazan-3-hydroximic halides." Chemistry of Heterocyclic Compounds 1992, 28 (5):581-585.

Horwitz KB et al. "Nuclear receptor coactivators and corepressors." Mol Endocrinol. Oct. 1996; 10(1):1167-77.

Kim JS et al. "Design of TATA box-binding protein/zinc finger fusions for targeted regulation of gene expression." Proc Natl Acad Sci U S A. Apr. 15, 1997; 94(8):3616-20.

Kirken RA et al. "Two discrete inteleukin-2 (IL2) receptor beta independently mediate IL2 activation of a PD98059/rapamycin/wortmannin-insnesitive Stat5a/b serine kinase." J Biol Chem. Jun. 13, 1997; 272(24):15459-65.

Nakagawa Y et al. "Quantitative structure-activity studies of insect growth regulators: XIX. Effects of substituents on the aromatic moiety of dibenzoylhydrazines on larvicidal activity against the beet armyworm *Spodoptera exigua*." Pest Manag Sci. Feb.;58(2):131-8.

O'Brien RN et al. "Structural and functional analysis of the human phosphoenolpyruvate carboxykinase gene promoter." Biochim Biophys Acta. Dec. 27, 1995; 1264(3):284-8.

Wing KD et al. "RH 5849, a Nonsteroldal Ecdysone Agonist: Effects on Larval Lepldoptera." Science. 1988, 241 (4864):470-472.

Spencer DM et al "Controlling signal transduction with synthetic ligands." Science. Nov. 12, 1993;262(5136):1019-24.

Trisyono A et al. "Effect of Nonsteroidal ecdysone agonists, methoxyfenozide and tebufenozide, on the European Corn Borer (Lepidoptera: Pytalidae)." J Economic Entomology 1997, 90:1486-1492.

Wurm FM et al. "Inducible overproduction of the mouse c-myc protein in mammalian cells." Proc Natl Acad Scie U S A. 1986, 83(15):5414-8.

Kumar M.B. et al. "A single point mutation in ecdysone receptor leads to increased ligand specificity: Implications for gene switch applications." Proc Natl Acad Scie U S A 2002, 99(23):14710-14715.

Tice C.M. et al. "Optimization of α-Acylaminoketone Ecdysone Agonists for Control of Gene Expression." Bioinorganic & Medicinal Chemistry Letters 13 (2003) 1883-1886.

Shimizu, B-i. et al., "Molting hormonal and larvicidal activities of aliphatic acyl analogs of dibenzoylhydrazine insecticides," *Steroids* 62:638-642, Elsevier Science Inc. (1997).

Talbot, W.S., et al., "Drosophila Tissues with Different Metamorphic Responses to Ecdysone Express Different Ecdysone Receptor Isoforms," *Cell* 73:1323-1337, Cell Press (1993).

Examiner's Score Search Results for U.S. Appl. No. 11/118,855, inventors Palli et al., filed Apr. 28, 2005, 27 pages (conducted on Aug. 14, 2007).

Examiner's Score Search Results for U.S. Appl. No. 11/118,855, inventors Palli et al., filed Apr. 28, 2005, 17 pages (conducted on Aug. 14, 2007).

Office Action mailed Jun. 13, 2005 in U.S. Appl. No. 09/965,703, inventors Palli, et al., filed Sep. 26, 2001.

Office Action mailed Nov. 24, 2004 in U.S. Appl. No. 09/965,703, inventors Palli, et al., filed Sep. 26, 2001.

Office Action mailed May 14, 2004 in U.S. Appl. No. 09/965,703, inventors Palli, et al., filed Sep. 26, 2001.

Office Action mailed Sep. 19, 2007 in U.S. Appl. No. 10/468,193, inventors Palli, et al., filed Dec. 17, 2003.

Office Action delivered electronically Mar. 13, 2008 in U.S. Appl. No. 10/468,199, inventors Kapitskaya, et al., filed Dec. 17, 2003.

Office Action mailed Jun. 11, 2007 in U.S. Appl. No. 10/468,199, inventors Kapitskaya, et al., filed Dec. 17, 2003.

Office Action mailed Oct. 26, 2006 in U.S. Appl. No. 10/468,199, inventors Kapitskaya, et al., filed Dec. 17, 2003.

Office Action mailed Sep. 7, 2007 in U.S. Appl. No. 11/118,855, inventors Palli, et al., filed Apr. 29, 2005.

Office Action delivered electronically Aug. 21, 2008 in U.S. Appl. No. 11/677,968, inventors Palli, et al., filed Feb. 22, 2007.

U.S. Appl. No. 10/468,199, inventors Kapitskaya, et al., filed Dec. 17, 2003, published as US 2004/0096942 A1.

U.S. Appl. No. 11/118,855, inventors Palli, et al., filed Apr. 28, 2005, published as US 2005/0266457 A1.

U.S. Appl. No. 10/468,193, inventors Palli, et al., filed Dec. 17, 2003, published as US 2006/0100416 A1.

U.S. Appl. No. 11/677,968, inventors Palli, et al., filed Feb. 22, 2007, published as US 2007/0161086 A1.

U.S. Appl. No. 11/841,529, inventors Palli, et al., filed Aug. 20, 2007, published as US 2007/0300313 A1.

U.S. Appl. No. 11/841,495, inventors Palli, et al., filed Aug. 20, 2007, published as 2008/0115237 A1.

U.S. Appl. No. 11/841,464, inventors Palli, et al., filed Aug. 20, 2007, published as US 2008/0145935 A1.

U.S. Appl. No. 11/841,597, inventors Kapitskaya, et al., filed Aug. 20, 2007, published as US 2008/0176280 A1.

U.S. Appl. No. 11/841,631, inventors Palli, et al., filed Aug. 20, 2007, published as US 2008/0216184 A1.

U.S. Appl. No. 10/468,200, inventors Palli, et al., filed Aug. 15, 2003.

U.S. Appl. No. 10/468,192, inventors Palli, et al., filed Aug. 15, 2003.

U.S. Appl. No. 11/841,644, inventors Palli, et al., filed Aug. 20, 2007.

U.S. Appl. No. 11/841,648, inventors Kapitskava, et al., filed Aug. 24, 2007.

U.S. Appl. No. 11/841,325, inventors Dhadialla, et al., filed Aug. 20, 2007, published as US 2008/0235816 A1.

Helmreich E.J.M., "The Biochemistry of Cell Signalling," p. 192, Oxford University Press (2001).

UniProtKB/Swiss-Protein Database, Accession No. P49880, "Ecdysone receptor," 2 pages (1996).

UniProtKB/Swiss-Protein Database, Accession No. P49883, "Ecdysone receptor," 2 pages (1996).

Office action mailed Mar. 22, 2010 in U.S. Appl. No. 11/841,648, inventors Kapitskaya et al., filed Aug. 24, 2007.

Notice of Allowance mailed Mar. 19, 2010 in U.S. Appl. No. 11/841,495, inventors Palli et al., filed on Aug. 20, 2007.

Notice of Allowance mailed Feb. 4, 2010 in U.S. Appl. No. 11/118,855, inventors Palli et al., filed Apr. 29, 2005.

Office Action mailed Apr. 1, 2010 in U.S. Appl. No. 11/841,529, inventors Palli et al., filed Aug. 20, 2007.

Office Action mailed Apr. 20, 2010 in U.S. Appl. No. 11/841,597, inventors Kapitskaya et al., filed Aug. 20, 2007.

U.S. Appl. No. 12/707,599, Inventors Dhadialla et al., filed Feb. 17, 2010.

Blumberg, B., et al., "Multiple retinoid-responsive receptors in a single cell: Families of retinoid "X" receptors and retinoic acid receptors in the *Xenopous* egg," *Proc. Natl. Acad. Sci. USA* 89:2321-2325, National Academy of Sciences, United States (1992).

Clayton, G.M., et al., "The structure of the ultraspiracle ligand-binding domain reveals a nuclear receptor locked in an inactive conformation," *Proc. Natl. Acad. Sci.* 98:1549-1554, National Academy of Sciences, United States (2001).

Laudet, V., et al., "A Unified Nomenclature System for the Nuclear Receptor Superfamily," *Cell* 97:161-163, Cell Press, United States (1999).

Mangelsdorf, D.J., et al., "Nuclear receptor that identifies a novel retinoic acid response pathway," *Nature* 345:224-229, Nature Publishing Group, England (1990).

Marklew, S., et al., "Isolation of a novel RXR from Xenopus that most closely resembles mammalian RXRβ and is expressed throughout early development," *Biochim Biophys Acta* 1218:267-272, Elsevier Science B.V., Netherlands (1994).

Palmer, M.J., et al., "Characterization of EcR and RXR Homologous in the Ixodid Tick, *Amblyomma amerianum* (L.)," *Am. Zool.* 39:747-757, American Society of Zoologists, United States (1999).

EMBL Nucleotide Sequence Database, Accession No. AJ251542, "Tenebrio molitor mRNA for USP protein," 7 pages (Feb. 15, 2000).

UniProtKB/Swiss-Protein Database, Accession No. O02035, "Ecdysone receptor," 6 pages (1997).

UniProtKB/Swiss-Protein Database, Accession No. O76246, "Ecdysteroid receptor," 6 pages (1998).

Hayward et al., "The sequence of *Locusta* RXR, homologous to *Drosophila* Ultraspiracle, and its evolutionary implications," *Development Genes Evolution* 209: 564-571, Springer-Verlag, United States (1999).

Hoffman et al., "Rapid retroviral delivery of tetracycline-inducible genes in a single autoregulatory cassette," *Proc. Natl. Acad. Sci. USA* 93: 5185-5190, National Academy of Sciences (1996).

Martinez et al., "Creation of ecdysone receptor chimeras in plants for controlled regulation of gene expression," *Molec. General Genetics* 261: 546-552, Springer-Verlag, United States (1999).

Office action mailed Aug. 22, 2006 in U.S. Appl. No. 10/239,134, inventors Palli et al., filed Sep. 19, 2002.

Office action mailed Jun. 29, 2009 in U.S. Appl. No. 11/841,648, inventors Kapitskaya et al., filed Aug. 24, 2007.

Office action mailed Feb. 22, 2010 in U.S. Appl. No. 11/837,834, inventors Palli et al., filed Aug. 13, 2007.

Office action mailed May 22, 2009 in U.S. Appl. No. 11/837,834, inventors Palli et al., filed Aug. 13, 2007.
Office action mailed Feb. 20, 2009 in U.S. Appl. No. 11/677,968, inventors Palli et al., filed Feb. 22, 2007.
Office Action mailed Feb. 24, 2009 in U.S. Application No. 11/841,495, inventors Palli et al., filed Aug. 20, 2007.
Office Action mailed Apr. 2, 2009 in U.S. Appl. No. 11/841,529, inventors Palli et al., filed Aug. 20, 2007.
Office action mailed Jun. 30, 2009 in U.S. Appl. No. 11/118,855, inventors Palli et al., filed Apr. 29, 2005.
Office Action mailed Feb. 25, 2009 in U.S. Appl. No. 11/841,325, inventors Dhadialla et al, filed Aug. 20, 2007.
Notice of Allowance mailed Dec. 24, 2009 in U.S. Appl. No. 11/841,325, inventors Dhadialla et al., filed Aug. 20, 2007.
Office Action mailed Feb. 18, 2010 in U.S. Appl. No. 10/468,193, inventors Palli et al., filed Dec. 17, 2003.
Office Action mailed Oct. 21, 2009 in U.S. Appl. No. 11/841,597, inventors Kapitskaya et al., filed Aug. 20, 2007.
U.S. Appl. No. 11/837,834, Inventors Palli et al., filed Aug. 13, 2007, published as US 2008/0064097 A1.
Office Action mailed Dec. 30, 2010 in U.S. Appl. No. 12/707,599, inventors Dhadialla et al., filed Feb. 17, 2010.
Office Action mailed Sep. 28, 2010 in U.S. Appl. No. 11/841,631, inventors Palli et al., filed Aug. 20, 2007.
Office Action mailed May 12, 2010 in U.S. Appl. No. 11/841,464, inventors Palli et al., filed Aug. 20, 2007.
Notice of Allowance mailed May 24, 2010 in U.S. Appl. No. 11/677,968, inventors Palli et al., filed Feb. 22, 2007.
Kumar, M.B., "A single point mutation in ecdysone receptor leads to increased ligand specificity: Implications for gene switch applications,"*Proc. Natl. Acad. Sci. 99*: 14710-14715, National Academy of Sciences, United States (2002).
Palli, S.R. et al., "Improved ecdysone receptor-based inducible gene regulation system,"*Eur. J. Biochem. 270*: 1308-1315, Wiley Interscience (2003).
Tran, H.T. et al., "Reconstruction of Ligand-Dependent Transactivation of *Choristoneura fumiferana* Ecdysone Receptor in Yeast," *Molecular Endocrinology 15*: 1140-1153, The Endocrine Society (2001).
Amendment and Reply Under 37 C.F.R. § 1.111 filed Jan. 21, 2010 in U.S. Appl. No. 11/841,597.
Amendment and Reply Under 37 C.F.R. § 1.114 filed Oct. 20, 2010 in U.S. Appl. No. 11/841,597.
U.S. Appl. No. 12/818,034, filed Jun. 17, 2010, inventors Palli et al.
U.S. Appl. No. 12/859,940, filed Aug. 20, 2010, inventors Palli et al.
Notice of Allowance mailed Dec. 27, 2010 in U.S. Appl. No. 11/118,855, inventors Palli et al., filed Apr. 29, 2005.
Notice of Allowance mailed Apr. 27, 2011 in U.S. Appl. No. 11/841,631, inventors Palli et al., filed Aug. 20, 2007.
Office Action mailed Sep. 14, 2010 in U.S. Appl. No. 11/841,644, inventors Palli et al., filed Aug. 20, 2007.
Office action mailed Dec. 7, 2010 in U.S. Appl. No. 11/841,648, inventors Kapitskaya et al., filed Aug. 24, 2007.
Office action mailed Nov. 10, 2010 in U.S. Appl. No. 11/841,597, inventors Kapitskaya et al., filed Aug. 20, 2007.
Office Action mailed Mar. 30, 2011, in U.S. Appl. No. 12/818,034, filed Jun. 17, 2010, inventors Palli et al.
Office Action mailed Dec. 30, 2010 in U.S. Appl. No. 12/707,599, inventors Dhadialla, et al., filed Feb. 17, 2010.
Office Action mailed Sep. 14, 2010, in U.S. Appl. No. 11/837,834., filed Aug. 13, 2007, inventors Palli et al.
Office Action mailed Jul. 20, 2011 in U.S. Appl. No. 12/707,599, inventors Dhadialla, et al., filed Feb. 17, 2010.

\* cited by examiner

SEQUENCE LISTING

```
<160> NUMBER OF SEQ ID NOS: 19

<210> SEQ ID NO 1
<211> LENGTH: 1878
<212> TYPE: DNA
<213> ORGANISM: Drosophila melanogaster

<400> SEQUENCE: 1
ggacctgcgc cacgggtgca agaggagctg tgcctggttt gcggcgacag ggcctccggc        60
taccactaca acgccctcac ctgtgagggc tgcaaggggt tctttcgacg cagcgttacg       120
aagagcgccg tctactgctg caagttcggg cgcgcctgcg aaatggacat gtacatgagg       180
cgaaagtgtc aggagtgccg cctgaaaaag tgcctggccg tgggtatgcg gccggaatgc       240
gtcgtcccgg agaaccaatg tgcgatgaag cggcgcgaaa agaaggccca gaaggagaag       300
gacaaaatga ccacttcgcc gagctctcag catggcggca atggcagctt ggcctctggt       360
ggcggccaag actttgttaa gaaggagatt cttgacctta tgacatgcga gccgcccag       420 catgccacta ttccgctact acctgatgaa atattggcca agtgtcaagc gcgcaatata       480
ccttccttaa cgtacaatca gttggccgtt atatacaagt taatttggta ccaggatggc       540
tatgagcagc catctgaaga ggatctcagg cgtataatga gtcaacccga tgagaacgag       600
agccaaacgg acgtcagctt tcggcatata accgagataa ccatactcac ggtccagttg       660
attgttgagt ttgctaaagg tctaccagcg tttacaaaga taccccagga ggaccagatc       720
acgttactaa aggcctgctc gtcggaggtg atgatgctgc gtatggcacg acgctatgac       780
cacagctcgg actcaatatt cttcgcgaat aatagatcat atacgcggga ttcttacaaa       840 atggccgaa tggctgataa cattgaagac ctgctgcatt tctgccgcca aatgttctcg       900
atgaaggtgg acaacgtcga atacgcgctt ctcactgcca ttgtgatctt ctcggaccgg       960
ccgggcctgg agaaggccca actagtcgaa gcgatccaga gctactacat cgacacgcta      1020
cgcatttata tactcaaccg ccactgcggc gactcaatga gcctcgtctt ctacgcaaag      1080
ctgctctcga tcctcaccga gctgcgtacg ctgggcaacc agaacgccga tgtgttc        1140 tcactaaagc tcaaaaaccg caaactgccc aagttcctcg aggagatctg ggacgttcat      1200
gccatcccgc catcggtcca gtcgcacctt cagattaccc aggaggagaa cgagcgtctc      1260
gagcgggctg agcgtatgcg ggcatcggtt gggggcgcca ttaccgccgg cattgattgc      1320
gactctgcct ccacttcggc ggcggcagcc gcggcccagc atcagcctca gcctcagccc      1380
cagccccaac cctcctccct gacccagaac gattcccagc accagacaca gccgcagcta      1440
caacctcagc taccacctca gctgcaaggt caactgcaac cccagctcca accacagctt      1500
```

```
cagacgcaac tccagccaca gattcaacca cagccacagc tccttcccgt ctccgctccc     1560
gtgcccgcct ccgtaaccgc acctggttcc ttgtccgcgg tcagtacgag cagcgaatac     1620
atgggcggaa gtgcggccat aggacccatc acgccggcaa ccaccagcag tatcacggct     1680
gccgttaccg ctagctccac cacatcagcg gtaccgatgg caacggagt tggagtcggt      1740 gttggggtgg gcggcaacgt cagcatgtat gcgaacgccc agacggcgat ggccttgatg     1800
ggtgtagccc tgcattcgca ccaagagcag cttatcgggg gagtggcggt taagtcggag     1860
cactcgacga ctgcatag                                                   1878

<210> SEQ ID NO 2
<211> LENGTH: 441
<212> TYPE: DNA
<213> ORGANISM: Saccharomyces cerevisiae

<400> SEQUENCE: 2
atgaagctac tgtcttctat cgaacaagca tgcgatattt gccgacttaa aaagctcaag       60
tgctccaaag aaaaaccgaa gtgcgccaag tgtctgaaga caactgggga gtgtcgctac      120
tctcccaaaa ccaaaaggtc tccgctgact agggcacatc tgacagaagt ggaatcaagg      180
ctagaaagac tggaacagct atttctactg atttttcctc gagaagacct tgacatgatt      240
ttgaaaatgg attctttaca ggatataaaa gcattgttaa caggattatt tgtacaagat      300
aatgtgaata aagatgccgt cacagataga ttggcttcag tggagactga tatgcctcta      360
acattgagac agcatagaat aagtgcgaca tcatcatcgg aagagagtag taacaaaggt      420
caaagacagt tgactgtatc g                                                441

<210> SEQ ID NO 3
<211> LENGTH: 750
<212> TYPE: DNA
<213> ORGANISM: cytomegalovirus

<400> SEQUENCE: 3
tcaatattgg ccattagcca tattattcat tggttatata gcataaatca atattggcta       60
ttggccattg catacgttgt atctatatca taatatgtac atttatattg gctcatgtcc      120
aatatgaccg ccatgttggc attgattatt gactagttat taatagtaat caattacggg      180
gtcattagtt catagcccat atatggagtt ccgcgttaca taacttacgg taaatggccc      240
gcctggctga ccgcccaacg acccccgccc attgacgtca ataatgacgt atgttcccat      300
agtaacgcca atagggactt tccattgacg tcaatgggtg gagtatttac ggtaaactgc      360
ccacttggca gtacatcaag tgtatcatat gccaagtccg cccctattg acgtcaatga      420 cggtaaatgg cccgcctggc attatgccca gtacatgacc ttacgggact ttcctacttg      480
gcagtacatc tacgtattag tcatcgctat taccatggtg atgcggtttt ggcagtacac      540
caatgggcgt ggatagcggt ttgactcacg gggatttcca gtctccacc ccattgacgt      600 caatgggagt ttgttttggc accaaaatca acgggacttt ccaaaatgtc gtaacaactg      660
cgatcgcccg ccccgttgac gcaaatgggc ggtaggcgtg tacggtggga ggtctatata      720
agcagagctc gtttagtgaa ccgtcagatc                                       750

<210> SEQ ID NO 4
<211> LENGTH: 1290
<212> TYPE: DNA
<213> ORGANISM: Choristoneura fumiferana

<400> SEQUENCE: 4
```

| | | | | |
|---|---|---|---|---|
| agaagggccc | tgctgaccgt | cagcaagagg | aactgtgtct | ggtatgcggg gacagagcct | 60 |
| ccggatacca | ctacaatgcg | ctcacgtgtg | aagggtgtaa | agggttcttc agacggagtg | 120 |
| ttaccaaaaa | tgcggtttat | atttgtaaat | tcggtcacgc | ttgcgaaatg acatgtaca | 180 |
| tgcgacggaa | atgccaggag | tgccgcctga | agaagtgctt | agctgtaggc atgaggcctg | 240 |
| agtgcgtagt | acccgagact | cagtgcgcca | tgaagcggaa | agagaagaaa gcacagaagg | 300 |
| agaaggacaa | actgcctgtc | agcacgacga | cggtggacga | ccacatgccg cccattatgc | 360 |
| agtgtgaacc | tccacctcct | gaagcagcaa | ggattcacga | agtggttcca aggtttctct | 420 |
| ccgacaagct | gttggagaca | aaccggcaga | aaaacatccc | ccagttgaca gccaaccagc | 480 |
| agttccttat | cgccaggctc | atctggtacc | aggacgggta | cgagcagcct tctgatgaag | 540 |
| atttgaagag | gattacgcag | acgtggcagc | aagcggacga | tgaaaacgaa gagtctgaca | 600 |
| ctccccttccg | ccagatcaca | gagatgacta | tcctcacggt | ccaacttatc gtggagttcg | 660 |
| cgaagggatt | gccagggttc | gccaagatct | cgcagcctga | tcaaattacg ctgcttaagg | 720 |
| cttgctcaag | tgaggtaatg | atgctccgag | tcgcgcgacg | atacgatgcg gcctcagaca | 780 |
| gtgttctgtt | cgcgaacaac | caagcgtaca | ctcgcgacaa | ctaccgcaag gctggcatgg | 840 |
| cctacgtcat | cgaggatcta | ctgcacttct | gccggtgcat | gtactctatg gcgttggaca | 900 |
| acatccatta | cgcgctgctc | acggctgtcg | tcatctttc | tgaccggcca ggggtggagc | 960 |
| agccgcaact | ggtggaagaa | atccagcggt | actacctgaa | tacgctccgc atctatatcc | 1020 |
| tgaaccagct | gagcgggtcg | cgcgcgttcgt | ccgtcatata | cggcaagatc ctctcaatcc | 1080 |
| tctctgagct | acgcacgctc | ggcatgcaaa | actccaacat | gtgcatctcc ctcaagctca | 1140 |
| agaacagaaa | gctgccgcct | ttcctcgagg | agatctggga | tgtggcagga catgtcgcac | 1200 |
| acccaaccgc | cgcctatctc | gagtccccca | cgaatctcta | gcccctgcgc gcacgcatcg | 1260 |
| ccgatgccgc | gtccggccgc | gctgctctga | | | 1290 |

<210> SEQ ID NO 5
<211> LENGTH: 606
<212> TYPE: DNA
<213> ORGANISM: Escherichia coli

<400> SEQUENCE: 5

| | | | | |
|---|---|---|---|---|
| atgaaagcgt | taacggccag | gcaacaagag | gtgtttgatc | tcatccgtga tcacatcagc | 60 |
| cagacaggta | tgccgccgac | gcgtgcggaa | atcgcgcagc | gtttggggtt ccgttcccca | 120 |
| aacgcggctg | aagaacatct | gaaggcgctg | gcacgcaaag | gcgttattga aattgtttcc | 180 |
| ggcgcatcac | gcgggattcg | tctgttgcag | gaagaggaag | aagggttgcc gctggtaggt | 240 |
| cgtgtggctg | ccggtgaacc | acttctggcg | caacagcata | ttgaaggtca ttatcaggtc | 300 |
| gatccttcct | tattcaagcc | gaatgctgat | ttcctgctgc | gcgtcagcgg gatgtcgatg | 360 |
| aaagatatcg | gcattatgga | tggtgacttg | ctggcagtgc | ataaaactca ggatgtacgt | 420 |
| aacggtcagg | tcgttgtcgc | acgtattgat | gacgaagtta | ccgttaagcg cctgaaaaaa | 480 |
| cagggcaata | aagtcgaact | gttgccagaa | aatagcgagt | ttaaaccaat tgtcgtagat | 540 |
| cttcgtcagc | agagcttcac | cattgaaggg | ctggcggttg | gggttattcg caacggcgac | 600 |
| tggctg | | | | | 606 |

<210> SEQ ID NO 6
<211> LENGTH: 711
<212> TYPE: DNA
<213> ORGANISM: Artificial Sequence
<220> FEATURE:

<223> OTHER INFORMATION: Chimeric MmRXR/LmUSP-EF

<400> SEQUENCE: 6

```
gccaacgagg acatgcctgt agagaagatt ctggaagccg agcttgctgt cgagcccaag      60
actgagacat acgtggaggc aaacatgggg ctgaacccca gctcaccaaa tgaccctgtt     120
accaacatct gtcaagcagc agacaagcag ctcttcactc ttgtggagtg ggccaagagg     180
atcccacact tttctgagct gcccctagac gaccaggtca tcctgctacg ggcaggctgg     240
aacgagctgc tgatcgcctc cttctcccac cgctccatag ctgtgaaaga tgggattctc     300
ctggccaccg gcctgcacgt acaccggaac agcgctcaca gtgctggggt gggcgccatc     360
tttgacaggg tgctaacaga gctggtgtct aagatgcgtg acatgcagat ggacaagact     420
gaacttggct gcttgcgatc tgttattctt ttcaatccag aggtgagggg tttgaaatcc     480
gcccaggaag ttgaacttct acgtgaaaaa gtatatgccg ctttggaaga atatactaga     540
acaacacatc ccgatgaacc aggaagattt gcaaaacttt tgcttcgtct gccttcttta     600
cgttccatag gccttaagtg tttggagcat ttgtttttct ttcgccttat tggagatgtt     660
ccaattgata cgttcctgat ggagatgctt gaatcacctt ctgattcata a              711
```

<210> SEQ ID NO 7
<211> LENGTH: 681
<212> TYPE: DNA
<213> ORGANISM: herpes simplex virus 7

<400> SEQUENCE: 7

```
atgggcccta aaagaagaa gcgtaaggtc aaagcgttaa cggccaggct tgaattaatt      60
ccgggcggaa tgaaagcgtt aacggccagg caacaagagg tgtttgatct catccgtgat     120
cacatcagcc agacaggtat gccgccgacg cgtgcggaaa tcgcgcagcg tttggggttc     180
cgttccccaa acgcggctga agaacatctg aaggcgctgg cacgcaaagg cgttattgaa     240
attgtttccg gcgcatcacg cgggattcgt ctgttgcagg aagaggaaga agggttgccg     300
ctggtaggtc gtgtggctgc cggtgaacca cttctggcgc aacagcatat tgaaggtcat     360
tatcaggtcg atccttcctt attcaagccg aatgctgatt tcctgctgcg cgtcagcggg     420
atgtcgatga agatatcgg cattatggat ggtgacttgc tggcagtgca taaaactcag     480
gatgtacgta acggtcaggt cgttgtcgca cgtattgatg acgaagttac cgttaagcgc     540
ctgaaaaaac agggcaataa agtcgaactg ttgccagaaa atagcgagtt taaaccaatt     600
gtcgtagatc ttcgtcagca gagcttcacc attgaagggc tggcggttgg ggttattcgc     660
aacggcgact ggctggaatt c                                                681
```

<210> SEQ ID NO 8
<211> LENGTH: 117
<212> TYPE: DNA
<213> ORGANISM: Saccharomyces cerevisiae

<400> SEQUENCE: 8

```
gcggagtact gtcctccgag cggagtactg tcctccgagc ggagtactgt cctccgagcg      60
gagtactgtc ctccgagcgg agtactgtcc tccgagcgga gtactgtcct ccgagcg        117
```

<210> SEQ ID NO 9
<211> LENGTH: 138
<212> TYPE: DNA
<213> ORGANISM: Mus musculus

<400> SEQUENCE: 9

| | | |
|---|---|---|
| atcttttgtt gactaagtca ataatcagaa tcagcaggtt tggagtcagc ttggcaggga | 60 |
| tcagcagcct gggttggaag gagggggtat aaaagccccct tcaccaggag aagccgtcac | 120 |
| acagatccac aagctcct | 138 |

<210> SEQ ID NO 10
<211> LENGTH: 1560
<212> TYPE: DNA
<213> ORGANISM: Homo sapiens

<400> SEQUENCE: 10

| | |
|---|---|
| atgctgctgc tgctgctgct gctgggcctg aggctacagc tctccctggg catcatccca | 60 |
| gttgaggagg agaacccgga cttctggaac cgcgaggcag ccgaggccct gggtgccgcc | 120 |
| aagaagctgc agcctgcaca gacagccgcc aagaacctca tcatcttcct gggcgatggg | 180 |
| atgggggtgt ctacggtgac agctgccagg atcctaaaag ggcagaagaa ggacaaactg | 240 |
| gggcctgaga taccctggc catgaccgc ttcccatatg tggctctgtc caagacatac | 300 |
| aatgtagaca aacatgtgcc agacagtgga gccacagcca cggcctacct gtgcggggtc | 360 |
| aagggcaact tccagaccat tggcttgagt gcagccgccc gctttaacca gtgcaacacg | 420 |
| acacgcggca acgaggtcat ctccgtgatg aatcgggcca agaaagcagg gaagtcagtg | 480 |
| ggagtggtaa ccaccacacg agtgcagcac gcctcgccag ccggcaccta cgcccacacg | 540 |
| gtgaaccgca actggtactc ggacgccgac gtgcctgcct cggcccgcca ggaggggtgc | 600 |
| caggacatcg ctacgcagct catctccaac atggacattg acgtgatcct aggtggaggc | 660 |
| cgaaagtaca tgtttcgcat gggaaccca gaccctgagt acccagatga ctacagccaa | 720 |
| ggtgggacca ggctgacgg gaagaatctg gtgcaggaat ggctggcgaa gcgccagggt | 780 |
| gcccggtatg tgtggaaccg cactgagctc atgcaggctt ccctggaccc gtctgtgacc | 840 |
| catctcatgg gtctctttga gcctggagac atgaaatacg agatccaccg agactccaca | 900 |
| ctggaccccct ccctgatgga gatgacagag gctgccctgc cctgctgag caggaacccc | 960 |
| cgcggcttct tcctcttcgt ggagggtggt cgcatcgacc atggtcatca tgaaagcagg | 1020 |
| gcttaccggg cactgactga gacgatcatg ttcgacgacg ccattgagag ggcgggccag | 1080 |
| ctcaccagcg aggaggacac gctgagcctc gtcactgccg accactccca cgtcttctcc | 1140 |
| ttcggaggct acccctgcg agggagctcc atcttcgggc tggccccctgg caaggcccgg | 1200 |
| gacaggaagg cctacacggt cctcctatac ggaaacggtc caggctatgt gctcaaggac | 1260 |
| ggcgcccggc cggatgttac cgagagcgag agcgggagcc ccgagtatcg gcagcagtca | 1320 |
| gcagtgcccc tggacgaaga gacccacgca ggcgaggacg tggcggtgtt cgcgcgcggc | 1380 |
| ccgcaggcgc acctggttca cggcgtgcag gagcagacct tcatagcgca cgtcatggcc | 1440 |
| ttcgccgcct gcctggagcc ctacaccgcc tgcgacctgg cgcccccgc cggcaccacc | 1500 |
| gacgccgcgc acccgggtta ctctagagtc ggggcggccg ccgcttcga gcagacatga | 1560 |

<210> SEQ ID NO 11
<211> LENGTH: 206
<212> TYPE: DNA
<213> ORGANISM: Escherichia coli

<400> SEQUENCE: 11

| | |
|---|---|
| aagcttgcat gcctgcaggt ccaggtccat atctaatctt acctcgactg ctgtatataa | 60 |
| aaccagtggt tatatgtaca gtactgctgt atataaaacc agtggttata tgtacagtac | 120 |
| gtcgactgct gtatataaaa ccagtggtta tatgtacagt actgctgtat ataaaaccag | 180 |

| tggttatatg tacagtacgt cgactc | 206 |

<210> SEQ ID NO 12
<211> LENGTH: 30
<212> TYPE: DNA
<213> ORGANISM: Artificial Sequence
<220> FEATURE:
<223> OTHER INFORMATION: Synthetic TATAA

<400> SEQUENCE: 12

| tagagggtat ataatggatc cccgggtacc | 30 |

<210> SEQ ID NO 13
<211> LENGTH: 1705
<212> TYPE: DNA
<213> ORGANISM: Photinus pyralis

<400> SEQUENCE: 13

| atggaagacg ccaaaaacat aaagaaaggc ccggcgccat tctatcctct agaggatgga | 60 |
| accgctggag agcaactgca taaggctatg aagagatacg ccctggttcc tggaacaatt | 120 |
| gcttttacag atgcacatat cgaggtgaac atcacgtacg cggaatactt cgaaatgtcc | 180 |
| gttcggttgg cagaagctat gaaacgatat gggctgaata caaatcacag aatcgtcgta | 240 |
| tgcagtgaaa actctcttca attctttatg ccggtgttgg gcgcgttatt tatcggagtt | 300 |
| gcagttgcgc ccgcgaacga catttataat gaacgtgaat tgctcaacag tatgaacatt | 360 |
| tcgcagccta ccgtagtgtt tgtttccaaa aaggggttgc aaaaaatttt gaacgtgcaa | 420 |
| aaaaaattac caataatcca gaaaattatt atcatggatt ctaaaacgga ttaccaggga | 480 |
| tttcagtcga tgtacacgtt cgtcacatct catctacctc ccggttttaa tgaatacgat | 540 |
| tttgtaccag agtcctttga tcgtgacaaa acaattgcac tgataatgaa ttcctctgga | 600 |
| tctactgggt tacctaaggg tgtggcccct ccgcatagaa ctgcctgcgt cagattctcg | 660 |
| catgccagag atcctatttt tggcaatcaa atcattccgg atactgcgat tttaagtgtt | 720 |
| gttccattcc atcacggttt tggaatgttt actacactcg atatttgat atgtggattt | 780 |
| cgagtcgtct taatgtatag atttgaagaa gagctgtttt tacgatccct tcaggattac | 840 |
| aaaattcaaa gtgcgttgct agtaccaacc ctattttcat tcttcgccaa aagcactctg | 900 |
| attgacaaat acgatttatc taatttacac gaaattgctt ctgggggcgc acctctttcg | 960 |
| aaagaagtcg gggaagcggt tgcaaaacgc ttccatcttc cagggatacg acaaggatat | 1020 |
| gggctcactg agactacatc agctattctg attacacccg agggggatga taaaccgggc | 1080 |
| gcggtcggta agttgttcc attttttgaa gcgaaggttg tggatctgga taccgggaaa | 1140 |
| acgctgggcg ttaatcagag aggcgaatta tgtgtcagag acctatgat tatgtccggt | 1200 |
| tatgtaaaca atccggaagc gaccaacgcc ttgattgaca aggatggatg gctacattct | 1260 |
| ggagacatag cttactggga cgaagacgaa cacttcttca tagttgaccg cttgaagtct | 1320 |
| ttaattaaat acaaaggata tcaggtggcc cccgctgaat tggaatcgat attgttacaa | 1380 |
| caccccaaca tcttcgacgc gggcgtggca ggtcttcccg acgatgacgc cggtgaactt | 1440 |
| cccgccgccg ttgttgtttt ggagcacgga aagacgatga cggaaaaaga tcgtggat | 1500 |
| tacgtcgcca gtcaagtaac aaccgcgaaa aagttgcgcg gaggagttgt gtttgtggac | 1560 |
| gaagtaccga aaggtcttac cggaaaactc gacgcaagaa aaatcagaga gatcctcata | 1620 |
| aaggccaaga agggcggaaa gtccaaattg taaaatgtaa ctgtattcag cgatgacgaa | 1680 |
| attcttagct attgtaatac tctag | 1705 |

<210> SEQ ID NO 14
<211> LENGTH: 1073
<212> TYPE: DNA
<213> ORGANISM: Choristoneura fumiferana

<400> SEQUENCE: 14

| | | | | | |
|---|---|---|---|---|---|
| cctgagtgcg | tagtacccga | gactcagtgc | gccatgaagc | ggaaagagaa | gaaagcacag | 60 |
| aaggagaagg | acaaactgcc | tgtcagcacg | acgacggtgg | acgaccacat | gccgcccatt | 120 |
| atgcagtgtg | aacctccacc | tcctgaagca | gcaaggattc | acgaagtggt | tccaaggttt | 180 |
| ctctccgaca | agctgttgga | gacaaaccgg | cagaaaaaca | tcccccagtt | gacagccaac | 240 |
| cagcagttcc | ttatcgccag | gctcatctgg | taccaggacg | ggtacgagca | gccttctgat | 300 |
| gaagatttga | gaggattac | gcagacgtgg | cagcaagcgg | acgatgaaaa | cgaagagtct | 360 |
| gacactccct | tccgccagat | cacagagatg | actatcctca | cggtccaact | tatcgtggag | 420 |
| ttcgcgaagg | gattgccagg | gttcgccaag | atctcgcagc | ctgatcaaat | tacgctgctt | 480 |
| aaggcttgct | caagtgaggt | aatgatgctc | cgagtcgcca | gatacgatgc | ggcctcagac | 540 |
| agtgttctgt | tcgcgaacaa | ccaagcgtac | actcgcgaca | actaccgcaa | ggctggcatg | 600 |
| gcctacgtca | tcgaggatct | actgcacttc | tgccggtgca | tgtactctat | ggcgttggac | 660 |
| aacatccatt | acgcgctgct | cacggctgtc | gtcatctttt | ctgaccggcc | agggttggag | 720 |
| cagccgcaac | tggtggaaga | atccagcgg | tactacctga | atacgctccg | catctatatc | 780 |
| ctgaaccagc | tgagcgggtc | ggcgcgttcg | tccgtcatat | acggcaagat | cctctcaatc | 840 |
| ctctctgagc | tacgcacgct | cggcatgcaa | aactccaaca | tgtgcatctc | cctcaagctc | 900 |
| aagaacagaa | agctgccgcc | tttcctcgag | gagatctggg | atgtggcagg | acatgtcgca | 960 |
| cacccaaccg | ccgcctatct | cgagtccccc | acgaatctct | agccctgcg | cgcacgcatc | 1020 |
| gccgatgccg | cgtccggccg | cgctgctctg | agaattcgat | atcaagcttc | tag | 1073 |

<210> SEQ ID NO 15
<211> LENGTH: 1109
<212> TYPE: DNA
<213> ORGANISM: Nephotetix cincticeps

<400> SEQUENCE: 15

| | | | | | |
|---|---|---|---|---|---|
| caggaggagc | tctgcctgtt | gtgcggagac | cgagcgtcgg | gataccacta | caacgctctc | 60 |
| acctgcgaag | gatgcaaggg | cttctttcgg | aggagtatca | ccaaaaacgc | agtgtaccag | 120 |
| tccaaatacg | gcaccaattg | tgaaatagac | atgtatatgc | ggcgcaagtg | ccaggagtgc | 180 |
| cgactcaaga | agtgcctcag | tgtagggatg | aggccagaat | gtgtagtacc | tgagtatcaa | 240 |
| tgtgccgtaa | aaggaaaga | gaaaaaagct | caaaaggaca | agataaaacc | tgtctcttca | 300 |
| accaatggct | cgcctgaaat | gagaatagac | caggacaacc | gttgtgtggt | gttgcagagt | 360 |
| gaagacaaca | ggtacaactc | gagtacgccc | agtttcggag | tcaaaccct | cagtccagaa | 420 |
| caagaggagc | tcatccacag | gctcgtctac | ttccagaacg | agtacgaaca | ccctgccgag | 480 |
| gaggatctca | gcggatcga | gaacctcccc | tgtgacgacg | atgacccgtg | tgatgttcgc | 540 |
| tacaaacaca | ttacggagat | cacaatactc | acagtccagc | tcatcgtgga | gtttgcgaaa | 600 |
| aaactgcctg | gtttcgacaa | actactgaga | gaggaccaga | tcgtgttgct | caaggcgtgt | 660 |
| tcgagcgagg | tgatgatgct | gcggatggcg | cggaggtacg | acgtccagac | agactcgatc | 720 |
| ctgttcgcca | acaaccagcc | gtacacgcga | gagtcgtaca | cgatggcagg | cgtggggga | 780 |
| gtcatcgaag | atctgctgcg | gttcggccga | ctcatgtgct | ccatgaaggt | ggacaatgcc | 840 |

-continued

```
gagtatgctc tgctcacggc catcgtcatc ttctccgagc ggccgaacct ggcggaagga      900
tggaaggttg agaagatcca ggagatctac ctggaggcgc tcaagtccta cgtggacaac      960
cgagtgaaac ctcgcagtcc gaccatcttc gccaaactgc tctccgttct caccgagctg     1020
cgaacactcg gcaaccagaa ctccgagatg tgcttctcgt taaactacgc aaccgcaaac     1080
atgccaccgt tcctcgaaga aatctggga                                       1109
```

<210> SEQ ID NO 16
<211> LENGTH: 714
<212> TYPE: DNA
<213> ORGANISM: Mus musculus

<400> SEQUENCE: 16

```
gccaacgagg acatgcctgt agagaagatt ctggaagccg agcttgctgt cgagcccaag       60
actgagacat acgtggaggc aaacatgggg ctgaacccca gctcaccaaa tgaccctgtt      120
accaacatct gtcaagcagc agacaagcag ctcttcactc ttgtggagtg ggccaagagg      180
atcccacact tttctgagct gccccctagac gaccaggtca tcctgctacg ggcaggctgg      240
aacgagctgc tgatcgcctc cttctcccac cgctccatag ctgtgaaaga tgggattctc      300
ctggccaccg gcctgcacgt acaccggaac agcgctcaca gtgctggggt gggcgccatc      360
tttgacaggg tgctaacaga gctggtgtct aagatgcgtg acatgcagat ggacaagacg      420
gagctgggct gcctgcgagc cattgtcctg ttcaaccctg actctaaggg gctctcaaac      480
cctgctgagg tggaggcgtt gagggagaag gtgtatgcgt cactagaagc gtactgcaaa      540
cacaagtacc ctgagcagcc gggcaggttt gccaagctgc tgctccgcct gcctgcactg      600
cgttccatcg ggctcaagtg cctggagcac ctgttcttct tcaagctcat cggggacacg      660
cccatcgaca ccttcctcat ggagatgctg gaggcaccac atcaagccac ctag            714
```

<210> SEQ ID NO 17
<211> LENGTH: 17
<212> TYPE: DNA
<213> ORGANISM: Artificial
<220> FEATURE:
<223> OTHER INFORMATION: Response element
<220> FEATURE:
<221> NAME/KEY: misc_feature
<222> LOCATION: (9)..(9)
<223> OTHER INFORMATION: n is a, c, g, or t

<400> SEQUENCE: 17

```
rrggttcant gacacyy                                                      17
```

<210> SEQ ID NO 18
<211> LENGTH: 13
<212> TYPE: DNA
<213> ORGANISM: Artificial
<220> FEATURE:
<223> OTHER INFORMATION: Response element
<220> FEATURE:
<221> NAME/KEY: misc_feature
<222> LOCATION: (7)..(7)
<223> OTHER INFORMATION: n is a, c, g, or t

<400> SEQUENCE: 18

```
aggtcanagg tca                                                          13
```

<210> SEQ ID NO 19
<211> LENGTH: 15
<212> TYPE: DNA
<213> ORGANISM: Artificial
<220> FEATURE:

```
<223> OTHER INFORMATION: Response element

<400> SEQUENCE: 19
gggttgaatg aattt                                                    15
```

MULTIPLE INDUCIBLE GENE REGULATION SYSTEM

RELATED APPLICATIONS

This application claims priority to U.S. provisional application Ser. No. 60/237,446, filed Oct. 3, 2000, which is incorporated herein by reference in its entirety.

FIELD OF THE INVENTION

This invention relates to the field of biotechnology or genetic engineering. More specifically, the present invention relates to a multiple inducible gene regulation system that functions within cells, tissues, or organisms to simultaneously control the quantitative expression of two or more genes.

BACKGROUND OF THE INVENTION

Various publications are cited herein, the disclosures of which are incorporated by reference in their entireties. However, the citation of any reference herein should not be construed as an admission that such reference is available as "Prior Art" to the instant application.

In the field of genetic engineering, precise control of gene expression is a valuable tool for studying, manipulating, and controlling development and other physiological processes. Gene expression is a complex biological process involving a number of specific protein-protein interactions. In order for gene expression to be triggered, such that it produces the RNA necessary as the first step in protein synthesis, a transcriptional activator must be brought into proximity of a promoter that controls gene transcription. Typically, the transcriptional activator itself is associated with a protein that has at least one DNA binding domain that binds to DNA binding sites present in the promoter regions of genes. Thus, for gene expression to occur, a protein comprising a DNA binding domain and a transactivation domain located at an appropriate distance from the DNA binding domain must be brought into the correct position in the promoter region of the gene.

The traditional transgenic approach utilizes a cell-type specific promoter to drive the expression of a designed transgene. A DNA construct containing the transgene is first incorporated into a host genome. When triggered by a transcriptional activator, expression of the transgene occurs in a given cell type.

A multiple gene regulation system is a system that allows the simultaneous and quantitative regulation of many different genes in the same cell, tissue, or organism. Currently, in applications that range from analyzing the human genome to proteomics to producing large-scale quantities of proteins, to gene therapies, there is no technology to regulate more than one gene at the same time in the same cell. Gene regulation is critical in all of these applications, because it ensures that whatever gene is being analyzed is controlled precisely and quantitatively, and therefore whatever results are obtained are tied directly and specifically to that gene, and not to others. Yet, gene regulation at present is limited to one gene at a time, and this is a significant qualitative and quantitative limitation. Parallel control of multiple genes in the same cell enables analysis of much more complex biological phenomena, where multiple genes are involved, as well as to create novel therapeutic applications.

Another means of regulating expression of foreign genes in cells is through inducible promoters. Examples of such promoters include the PR1-a promoter, prokaryotic repressor-operator systems, systems based on immunosuppressive molecules, and higher eukaryotic transcription activation systems.

The PR1-a promoter from tobacco is induced during the systemic acquired resistance response following pathogen attack. The use of PR1-a may be limited because it often responds to endogenous materials and external factors such as pathogens, UV-B radiation, and pollutants. Gene regulation systems based on promoters induced by heat shock, interferon and heavy metals have been described (Wurn et al., 1986, Proc. Natl. Acad. Sci. USA 83:5414-5418; Arnheiter et al., 1990 Cell 62:51-61; Filmus et al., 1992 Nucleic acids Research 20:27550-27560). However, these systems have limitations due to their effect on expression of non-target genes. These systems are also leaky.

Prokaryotic repressor-operator systems utilize bacterial repressor proteins and the unique operator DNA sequences to which they bind. Both the tetracycline ("Tet") and lactose ("Lac") repressor-operator systems from the bacterium *Escherichia coli* have been used in plants and animals to control gene expression. In the Tet system, tetracycline binds to the TetR repressor protein, resulting in a conformational change which releases the repressor protein from the operator which as a result allows transcription to occur. In the Lac system, a lac operon is activated in response to the presence of lactose, or synthetic analogs such as isopropyl-b-D-thiogalactoside. Unfortunately, the use of such systems is restricted by unstable chemistry of the ligands, i.e. tetracycline and lactose, their toxicity, their natural presence, or the relatively high levels required for induction or repression. For similar reasons, utility of such systems in animals is limited.

Immunosuppressive molecules such as FK506, rapamycin and cyclosporin A can bind to immunophilins FKBP12, cyclophilin etc. Using this information, a general strategy was devised to bring together any two proteins simply by placing FK506 on each of the two proteins or by placing FK506 on one and cyclosporin A on another one. A synthetic homodimer of FK506 (FK1012) or a compound resulted from fusion of FK506-cyclosporine (FKCsA) can then be used to induce dimerization of these molecules (Spencer et al., 1993, *Science* 262:1019-24; Belshaw et al., 1996 *Proc Natl Acad Sci USA* 93:4604-7). Gal4 DNA binding domain fused to FKBP12 and VP16 activator domain fused to cyclophilin, and FKCsA compound were used to show heterodimerization and activation of a reporter gene under the control of a promoter containing Gal4 binding sites. Unfortunately, this system includes immunosuppressants that can have unwanted side effects which limits its use for various mammalian gene regulation system applications.

Higher eukaryotic transcription activation systems such as steroid hormone receptor systems have also been employed. Steroid hormone receptors are members of the nuclear receptor superfamily and are found in vertebrate and invertebrate cells. Unfortunately, use of steroidal compounds that activate the receptors for the regulation of gene expression, particularly in plants and mammals, is limited due to their involvement in many other natural biological pathways in such organisms. In order to overcome such difficulties, an alternative system has been developed using insect ecdysone receptors (EcR).

The molecular target for ecdysone in insects consists of at least ecdysone receptor (EcR) and ultraspiracle protein (USP). EcR is a member of the nuclear steroid receptor super family that is characterized by signature DNA and ligand binding domains, and an activation domain (Koelle et al. 1991, Cell, 67:59-77). EcR is a member of the nuclear receptor superfamily and classified into subfamily 1, group H (referred to herein as "Group H nuclear receptors"). The members of each group share 40-60% amino acid identity in the E (ligand binding) domain (Laudet et al., A Unified Nomenclature System for the Nuclear Receptor Subfamily, 1999; Cell 97:161-163). In addition to the ecdysone receptor, other members of this nuclear receptor subfamily 1, group H include: ubiquitous receptor (UR), Orphan receptor 1 (OR-1), steroid hormone nuclear receptor 1 (NER-1), RXR interacting protein-15 (RIP-15), liver x receptor β (LXRβ, steroid hormone receptor like protein (RLD-1), liver x receptor (LXR), liver x receptor α (LXRα), farnesoid x receptor (FXR), receptor interacting protein 14 (RIP-14), and farnesol receptor (HRR-1).

EcR receptors are responsive to a number of steroidal compounds such as ponasterone A and muristerone A. Recently, non-steroidal compounds with ecdysteroid agonist activity have been described, including the commercially available insecticides tebufenozide and methoxyfenozide that are marketed world wide by Rohm and Haas Company (see International Patent Application No. PCT/EP96/00686 and U.S. Pat. No. 5,530,028). Both analogs have exceptional safety profiles to other organisms.

The insect ecdysone receptor (EcR) heterodimerizes with Ultraspiracle (USP), the insect homologue of the mammalian RXR, and binds ecdysteroids and ecdysone receptor response elements and activate transcription of ecdysone responsive genes (Riddiford et al. 2000, Vitam Horm. 60:1-73). The EcR/USP/ligand complexes play important roles during insect development and reproduction. The EcR is a member of the steroid hormone receptor superfamily and has five modular domains, A/B (transactivation), C (DNA binding, heterodimerization)), D (Hinge, heterodimerization), E (ligand binding, heterodimerization and transactivation and, in some cases, F (transactivation) domains. Some of these domains such as A/B, C and E retain their function when they are fused to other proteins.

Tightly regulated inducible gene expression systems or "gene switches" are useful for various applications such as gene therapy, large scale production of proteins in cells, cell based high throughput screening assays, functional genomics and regulation of traits in transgenic plants and animals. The first version of an EcR-based gene switch used *Drosophila melanogaster* EcR (DmEcR) and *Mus musculus* RXR (MmRXR) and showed that these receptors in the presence of steroid, ponasteroneA, transactivate reporter genes in mammalian cell lines and transgenic mice (Christopherson et al., (1992) PNAS, 89(14):6314-8 and No et al., (1996) PNAS, 98(8):3346-51). The EcR and tetracycline regulation systems were compared directly and it was concluded that the EcR regulation system has lower basal activity when compared to either of the two versions of the tetracycline-based system (tTA and rtTA) demonstrating that the EcR-based system is less leaky. Later, Suhr et al., (1998, PNAS 95:7999-8004) showed that non-steroidal ecdysone agonist, tebufenozide, induced high level of transactivation of reporter genes in mammalian cells through *Bombyx mori* EcR (BmEcR) in the absence of exogenous heterodimer partner [see also International Patent Application No. PCT/US98/14215 (WO 99/02683)].

International Patent Applications No. PCT/US97/05330 (WO 97/38117) and PCT/US99/08381 (WO99/58155) disclose methods for modulating the expression of an exogenous gene in which a DNA construct comprising the exogenous gene and an ecdysone response element is activated by a second DNA construct comprising an ecdysone receptor that, in the presence of a ligand therefor, and optionally in the presence of a receptor capable of acting as a silent partner, binds to the ecdysone response element to induce gene expression. The ecdysone receptor of choice was isolated from *Drosophila melanogaster*. Typically, such systems require the presence of the silent partner, preferably retinoid X receptor (RXR), in order to provide optimum activation. In mammalian cells, insect ecdysone receptor (EcR) heterodimerizes with retinoid X receptor (RXR) and regulates expression of target genes in a ligand dependent manner. International Patent Application No. PCT/US98/14215 (WO 99/02683) discloses that the ecdysone receptor isolated from the silk moth *Bombyx mori* is functional in mammalian systems without the need for an exogenous dimer partner.

U.S. Pat. No. 6,265,173 B1 discloses that various members of the steroid/thyroid superfamily of receptors can combine with *Drosophila melanogaster* ultraspiracle receptor (USP) or fragments thereof comprising at least the dimerization domain of USP for use in a gene expression system. U.S. Pat. No. 5,880,333 discloses a *Drosophila melanogaster* EcR and ultraspiracle (USP) heterodimer system used in plants in which the transactivation domain and the DNA binding domain are positioned on two different hybrid proteins. Unfortunately, these USP-based systems are constitutive in animal cells and therefore, are not effective for regulating reporter gene expression.

In each of these cases, the transactivation domain and the DNA binding domain (either as native EcR as in International Patent Application No. PCT/US98/14215 or as modified EcR as in International Patent Application No. PCT/US97/05330) were incorporated into a single molecule and the other heterodimeric partners, either USP or RXR, were used in their native state.

Drawbacks of the above described EcR-based gene regulation systems include a considerable background activity in the absence of ligands, non-applicability of these systems for use in both plants and animals (see U.S. Pat. No. 5,880,333), and limited use or inability to regulate expression of multiple genes. Therefore, a need exists in the art for improved EcR-based systems to precisely modulate the expression of two or more exogenous genes in both plants and animals. Such improved systems would be useful for applications such as gene therapy, large scale production of proteins and antibodies, cell-based high throughput screening assays, functional genomics and regulation of traits in transgenic animals. For certain applications such as gene therapy, it may be desirable to have an inducible gene expression system that responds well to synthetic non-steroid ligands and at the same is insensitive to the natural steroids.

Recently, Applicants have shown that an ecdysone receptor-based inducible gene expression system in which the transactivation and DNA binding domains are separated from each other by placing them on two different proteins results in greatly reduced background activity in the absence of a ligand and significantly increased activity over background in the presence of a ligand (pending application PCT/US01/09050, incorporated herein in its entirety by reference). This two-hybrid system is a significantly improved inducible gene expression modulation system compared to the two systems disclosed in applications PCT/US97/05330 and PCT/US98/14215. The two-hybrid system exploits the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283,173). Briefly, the two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, the interaction of the first polypeptide with the second polypeptide effectively tethers the DNA binding domain to the transactivation domain. Since the DNA binding and transactivation domains reside on two different molecules, the background activity in the absence of ligand is greatly reduced.

A two-hybrid system also provides improved sensitivity to non-steroidal ligands for example, diacylhydrazines, when compared to steroidal ligands for example, ponasterone A ("PonA") or muristerone A ("MurA"). That is, when compared to steroids, the non-steroidal ligands provide higher activity at a lower concentration. In addition, since transactivation based on EcR gene switches is often cell-line dependent, it is easier to tailor switching systems to obtain maximum transactivation capability for each application. Furthermore, the two-hybrid system avoids some side effects due to overexpression of RXR that often occur when unmodified RXR is used as a switching partner. In a preferred two-hybrid system, native DNA binding and transactivation domains of EcR or RXR are eliminated and as a result, these hybrid molecules have less chance of interacting with other steroid hormone receptors present in the cell resulting in reduced side effects.

Applicants' invention overcomes a deficiency in the art and provides a means to simultaneously modulate expression of two or more genes in the same cell. Applicants' invention provides a multiple inducible gene regulation system that allows the simultaneous and quantitative regulation of two or more different genes in the same cell, tissue, or organism. Applicants' invention is useful in applications in which multiple gene regulation is critical. Thus, Applicants' invention overcomes a deficiency in the field of gene expression and is useful in the fields of functional genomics, proteomics, metabolomics, toxicology screening, cell-based high-throughput screening assays, protein production, gene therapies, and the like. Applicants' invention provides a means for parallel control of multiple genes in the same cell and enables one of skill in the art to analyze complex biological phenomena, where multiple genes or pathways are involved, as well as to create novel therapeutic applications.

DETAILED DESCRIPTION OF THE INVENTION

Figure 1A:
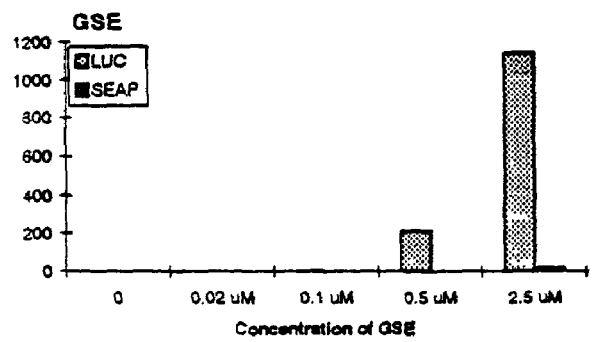
FIG. 1: Orthogonal transactivation of reporter genes through GAL4DmEcR-CDEF and LexACfEcR-CDEF constructs transfected into NIH3T3 cells along with VP16MmRXRα-LmUSP-EFchimera, p8OPLexARELuc, and p6XGALRETTPSEAP by PonA and/or GS™-E. The numbers on top of the bars indicate fold increase over DMSO levels.

The present invention is useful for applications such as gene therapy, large scale production of proteins and antibodies, cell-based high throughput screening assays, orthogonal ligand screening assays, functional genomics, proteomics, metabolomics, toxicology screening, and regulation of traits in transgenic organisms, where control of gene expression levels is desirable. An advantage of Applicants' invention is that it provides a means to regulate expression of two or more genes and to tailor expression levels to suit the user's requirements.

DEFINITIONS

In this disclosure, a number of terms and abbreviations are used. The following definitions are provided and should be helpful in understanding the scope and practice of the present invention.

In a specific embodiment, the term "about" or "approximately" means within 20%, preferably within 10%, more preferably within 5%, and even more preferably within 1% of a given value or range.

As used herein, all percentages are percent by weight and all parts are parts by weight, unless otherwise specified, and are inclusive and combinable. All ratios are by weight and all ratio ranges are inclusive and combinable. All molar ranges are inclusive and combinable.

The term "substantially free" means that a composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The term "isolated" for the purposes of the present invention designates a biological material (nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated". The term "purified" does not require the material to be present in a form exhibiting absolute purity, exclusive of the presence of other compounds. It is rather a relative definition.

A polynucleotide is in the "purified" state after purification of the starting material or of the natural material by at least one order of magnitude, preferably 2 or 3 and preferably 4 or 5 orders of magnitude.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes but is not limited to cDNA, genomic DNA, plasmids DNA, synthetic DNA, and semi-synthetic DNA. DNA may be linear, circular, or supercoiled.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester anologs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

The term "fragment" will be understood to mean a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least 6-1500 consecutive nucleotides of a polynucleotide according to the invention.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "gene" refers to an assembly of nucleotides that encode a polypeptide, and includes cDNA and genomic DNA nucleic acids. "Gene" also refers to a nucleic acid fragment that expresses a specific protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Heterologous" DNA refers to DNA not naturally located in the cell, or in a chromosomal site of the cell. Preferably, the heterologous DNA includes a gene foreign to the cell.

The term "genome" includes chromosomal as well as mitochondrial, chloroplast and viral DNA or RNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989 infra). Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization.

Stringency conditions can be adjusted to screen for moderately similar fragments, such as homologous sequences from distantly related organisms, to highly similar fragments, such as genes that duplicate functional enzymes from closely related organisms. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC.

Hybridization requires that the two nucleic acids contain complementary sequences, although depending on the stringency of the hybridization, mismatches between bases are possible. The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as disclosed or used herein as well as those substantially similar nucleic acid sequences.

In a specific embodiment of the invention, polynucleotides are detected by employing hybridization conditions comprising a hybridization step at $T_m$ of 55° C., and utilizing conditions as set forth above. In a preferred embodiment, the $T_m$ is 60° C.; in a more preferred embodiment, the $T_m$ is 63° C.; in an even more preferred embodiment, the $T_m$ is 65° C.

Post-hybridization washes also determine stringency conditions. One set of preferred conditions uses a series of washes starting with 6×SSC, 0.5% SDS at room temperature for 15 minutes (min), then repeated with 2×SSC, 0.5% SDS at 45° C. for 30 minutes, and then repeated twice with 0.2×SSC, 0.5% SDS at 50° C. for 30 minutes. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids comprise complementary sequences, although depending on the stringency of the hybridization, mismatches between bases are possible.

The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8).

In a specific embodiment of the invention, polynucleotides are detected by employing hybridization conditions comprising a hybridization step in less than 500 mM salt and at least 37 degrees Celsius, and a washing step in 2×SSPE at at least 63 degrees Celsius. In a preferred embodiment, the hybridization conditions comprise less than 200 mM salt and at least 37 degrees Celsius for the hybridization step. In a more preferred embodiment, the hybridization conditions comprise 2×SSPE and 63 degrees Celsius for both the hybridization and washing steps.

In one embodiment, the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "probe" refers to a single-stranded nucleic acid molecule that can base pair with a complementary single stranded target nucleic acid to form a double-stranded molecule.

As used herein, the term "oligonucleotide" refers to a nucleic acid, generally of at least 18 nucleotides, that is hybridizable to a genomic DNA molecule, a cDNA molecule, a plasmid DNA or an mRNA molecule. Oligonucleotides can be labeled, e.g., with $^{32}P$-nucleotides or nucleotides to which a label, such as biotin, has been covalently conjugated. A labeled oligonucleotide can be used as a probe to detect the presence of a nucleic acid. Oligonucleotides (one or both of which may be labeled) can be used as PCR primers, either for cloning full length or a fragment of a nucleic acid, or to detect the presence of a nucleic acid. An oligonucleotide can also be used to form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A "primer" is an oligonucleotide that hybridizes to a target nucleic acid sequence to create a double stranded nucleic acid region that can serve as an initiation point for DNA synthesis under suitable conditions. Such primers may be used in a polymerase chain reaction.

"Polymerase chain reaction" is abbreviated PCR and means an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

"Reverse transcription-polymerase chain reaction" is abbreviated RT-PCR and means an in vitro method for enzymatically producing a target cDNA molecule or molecules from an RNA molecule or molecules, followed by enzymatic amplification of a specific nucleic acid sequence or sequences within the target cDNA molecule or molecules as described above. RT-PCR also provides a means to detect the presence of the target molecule and, under quantitative or semi-quantitative conditions, to determine the relative amount of that target molecule within the starting pool of nucleic acids.

A DNA "coding sequence" is a double-stranded DNA sequence that is transcribed and translated into a polypeptide in a cell in vitro or in vivo when placed under the control of appropriate regulatory sequences. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure. The boundaries of the coding sequence are determined by a start codon at the 5' (amino) terminus and a translation stop codon at the 3' (carboxyl) terminus. A coding sequence can include, but is not limited to, prokaryotic sequences, cDNA from mRNA, genomic DNA sequences, and even synthetic DNA sequences. If the coding sequence is intended for expression in a eukaryotic cell, a polyadenylation signal and transcription termination sequence will usually be located 3' to the coding sequence.

"Open reading frame" is abbreviated ORF and means a length of nucleic acid sequence, either DNA, cDNA or RNA, that comprises a translation start signal or initiation codon, such as an ATG or AUG, and a termination codon and can be potentially translated into a polypeptide sequence.

The term "head-to-head" is used herein to describe the orientation of two polynucleotide sequences in relation to each other. Two polynucleotides are positioned in a head-to-head orientation when the 5' end of the coding strand of one polynucleotide is adjacent to the 5' end of the coding strand of the other polynucleotide, whereby the direction of transcription of each polynucleotide proceeds away from the 5' end of the other polynucleotide. The term "head-to-head" may be abbreviated (5')-to-(5') and may also be indicated by the symbols (← →) or (3'←5'5'→3').

The term "tail-to-tail" is used herein to describe the orientation of two polynucleotide sequences in relation to each other. Two polynucleotides are positioned in a tail-to-tail orientation when the 3' end of the coding strand of one polynucleotide is adjacent to the 3' end of the coding strand of the other polynucleotide, whereby the direction of transcription of each polynucleotide proceeds toward the other polynucleotide. The term "tail-to-tail" may be abbreviated (3')-to-(3') and may also be indicated by the symbols (→ ←) or (5'→3'3'←5').

The term "head-to-tail" is used herein to describe the orientation of two polynucleotide sequences in relation to each other. Two polynucleotides are positioned in a head-to-tail orientation when the 5' end of the coding strand of one polynucleotide is adjacent to the 3' end of the coding strand of the other polynucleotide, whereby the direction of transcription of each polynucleotide proceeds in the same direction as that of the other polynucleotide. The term "head-to-tail" may be abbreviated (5')-to-(3') and may also be indicated by the symbols (→ →) or (5'→3'5'→3').

The term "downstream" refers to a nucleotide sequence that is located 3' to reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" refer to an enzyme that binds and cuts within a specific nucleotide sequence within double stranded DNA.

"Homologous recombination" refers to the insertion of a foreign DNA sequence into another DNA molecule, e.g., insertion of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Several methods known in the art may be used to propagate a polynucleotide according to the invention. Once a suitable host system and growth conditions are established, recombinant expression vectors can be propagated and prepared in quantity. As described herein, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

A "vector" is any means for the cloning of and/or transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes both viral and nonviral means for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript vector. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include but are not limited to retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

The term "plasmid" refers to an extra chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" is a "replicon", which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector").

Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963-967; Wu and Wu, 1988, J. Biol. Chem. 263:14621-14624; and Hartmut et al., Canadian Patent Application No. 2,012,311, filed Mar. 15, 1990).

A polynucleotide according to the invention can also be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et al., 1987. PNAS 84:7413; Mackey, et al., 1988. Proc. Natl. Acad. Sci. U.S.A. 85:8027-8031; and Ulmer et al., 1993. Science 259:1745-1748). The use of cationic lipids may promote encapsulation of negatively charged nucleic acids, and also promote fusion with negatively charged cell membranes (Felgner and Ringold, 1989. Science 337:387-388). Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey, et al., 1988, supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al., 1992. Hum. Gene Ther. 3:147-154; and Wu and Wu, 1987. J. Biol. Chem. 262:4429-4432).

The term "transfection" means the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "genetic region" will refer to a region of a nucleic acid molecule or a nucleotide sequence that comprises a gene encoding a polypeptide.

In addition, the recombinant vector comprising a polynucleotide according to the invention may include one or more origins for replication in the cellular hosts in which their amplification or their expression is sought, markers or selectable markers.

The term "selectable marker" means an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" means a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes may also be considered reporter genes.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". Promoters that cause a gene to be expressed in a specific cell type are commonly referred to as "cell-specific promoters" or "tissue-specific promoters". Promoters that cause a gene to be expressed at a specific stage of development or cell differentiation are commonly referred to as "developmentally-specific promoters" or "cell differentiation-specific promoters". Promoters that are induced and cause a gene to be expressed following exposure or treatment of the cell with an agent, biological molecule, chemical, ligand, light, or the like that induces the promoter are commonly referred to as "inducible promoters" or "regulatable promoters". It is further recognized that since in most cases the exact boundaries of regulatory sequences have not been completely defined, DNA fragments of different lengths may have identical promoter activity.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

The term "response element" means one or more cis-acting DNA elements which confer responsiveness on a promoter mediated through interaction with the DNA-binding domains of the first chimeric gene. This DNA element may be either palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. The response element may comprise a minimal promoter isolated from different organisms depending upon the nature of the cell or organism into which the response element will be incorporated. The DNA binding domain of the first hybrid protein binds, in the presence or absence of a ligand, to the DNA sequence of a response element to initiate or suppress transcription of downstream gene(s) under the regulation of this response element. Examples of DNA sequences for response elements of the natural ecdysone receptor include RRGG/TTCANTGAC/ACYY (SEQ ID NO: 17) (see Cherbas L., et. al., (1991), *Genes Dev.* 5, 120-131); AGGT-CAN$_{(n)}$AGGTCA, where N$_{(n)}$ can be one or more spacer nucleotides (SEQ ID NO: 18) (see D'Avino PP., et. al., (1995), *Mol. Cell. Endocrinol*, 113, 1-9); and GGGTTGAAT-GAATTT (SEQ ID NO: 19) (see Antoniewski C., et. al., (1994). *Mol. Cell Biol.* 14, 4465-4474).

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from a nucleic acid or polynucleotide. Expression may also refer to translation of mRNA into a protein or polypeptide.

The terms "cassette", "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

For purposes of this invention, the term "gene switch" refers to the combination of a response element associated with a promoter, and an EcR based system which, in the presence of one or more ligands, modulates the expression of a gene into which the response element and promoter are incorporated.

The terms "modulate" and "modulates" mean to induce, reduce or inhibit nucleic acid or gene expression, resulting in the respective induction, reduction or inhibition of protein or polypeptide production.

The plasmids or vectors according to the invention may further comprise at least one promoter suitable for driving expression of a gene in a host cell. The term "expression vector" means a vector, plasmid or vehicle designed to enable the expression of an inserted nucleic acid sequence following transformation into the host. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving these genes is suitable for the present invention including but not limited to: viral promoters, bacterial promoters, animal promoters, mammalian promoters, synthetic promoters, constitutive promoters, tissue specific promoter, developmental specific promoters, inducible promoters, light regulated promoters; CYC1, HIS3, GAL1, GAL4, GAL10, ADH1, PGK, PHO5, GAPDH, ADC1, TRP1, URA3, LEU2, ENO, TPI, alkaline phosphatase promoters (useful for expression in *Saccharomyces*); AOX1 promoter (useful for expression in *Pichia*); b-lactamase, lac, ara, tet, trp, $1P_L$, $1P_R$, T7, tac, and trc promoters (useful for expression in *Escherichia coli*); light regulated-, seed specific-, pollen specific-, ovary specific-, pathogenesis or disease related-, cauliflower mosaic virus 35S, CMV 35S minimal, cassava vein mosaic virus (CsVMV), chlorophyll a/b binding protein, ribulose 1,5-bisphosphate carboxylase, shoot-specific, root specific, chitinase, stress inducible, rice tungro bacilliform virus, plant superpromoter, potato leucine aminopeptidase, nitrate reductase, mannopine synthase, nopaline synthase, ubiquitin, zein protein, and anthocyanin promoters (useful for expression in plant cells); animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, a baculovirus IE1 promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell α-actin, and the like. In addition, these expression sequences may be modified by addition of enhancer or regulatory sequences and the like.

Enhancers that may be used in embodiments of the invention include but are not limited to: an SV40 enhancer, a cytomegalovirus (CMV) enhancer, an elongation factor 1 (EF1) enhancer, yeast enhancers, viral gene enhancers, and the like.

Termination control regions, i.e., terminator or polyadenylation sequences, may also be derived from various genes native to the preferred hosts. Optionally, a termination site may be unnecessary, however, it is most preferred if included. In a preferred embodiment of the invention, the termination control region may be comprise or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Regulatory region" means a nucleic acid sequence that regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

A regulatory region from a "heterologous source" is a regulatory region that is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

A "polypeptide" is a polymeric compound comprised of covalently linked amino acid residues. Amino acids have the following general structure:

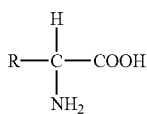

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. A polypeptide of the invention preferably comprises at least about 14 amino acids.

A "protein" is a polypeptide that performs a structural or functional role in a living cell.

An "isolated polypeptide" or "isolated protein" is a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

"Fragment" of a polypeptide according to the invention will be understood to mean a polypeptide whose amino acid sequence is shorter than that of the reference polypeptide and which comprises, over the entire portion with these reference polypeptides, an identical amino acid sequence. Such fragments may, where appropriate, be included in a larger polypeptide of which they are a part. Such fragments of a polypeptide according to the invention may have a length of at least 2-300 amino acids.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art. A variant polypeptide preferably comprises at least about 14 amino acids.

A "heterologous protein" refers to a protein not naturally produced in the cell.

A "mature protein" refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

The term "signal peptide" refers to an amino terminal polypeptide preceding the secreted mature protein. The signal peptide is cleaved from and is therefore not present in the mature protein. Signal peptides have the function of directing and translocating secreted proteins across cell membranes. Signal peptide is also referred to as signal protein.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

The term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667.). Such proteins (and their encoding genes) have sequence homology, as reflected by their high degree of sequence similarity. However, in common usage and in the instant application, the term "homologous," when modified with an adverb such as "highly," may refer to sequence similarity and not a common evolutionary origin.

Accordingly, the term "sequence similarity" in all its grammatical forms refers to the degree of identity or correspondence between nucleic acid or amino acid sequences of proteins that may or may not share a common evolutionary origin (see Reeck et al., 1987, Cell 50:667).

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Sambrook et al., 1989, supra.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Substantially similar nucleic acid fragments of the instant invention are those nucleic acid fragments whose DNA sequences are at least 70% identical to the DNA sequence of the nucleic acid fragments reported herein. Preferred substantially nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Even more preferred are nucleic acid fragments that are at least 95% identical to the DNA sequence of the nucleic acid fragments reported herein.

Two amino acid sequences are "substantially homologous" or "substantially similar" when greater than about 40% of the amino acids are identical, or greater than 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215: 403-410). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), and DNAS-TAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, two or more individually operable gene regulation systems are said to be "orthogonal" when; a) modulation of each of the given systems by its respective ligand, at a chosen concentration, results in a measurable change in the magnitude of expression of the gene of that system, and b) the change is statistically significantly different than the change in expression of all other systems simultaneously operable in the cell, tissue, or organism, regardless of the simultaneity or sequentially of the actual modulation. Preferably, modulation of each individually operable gene regulation system effects a change in gene expression at least 2-fold greater than all other operable systems in the cell, tissue, or organism. More preferably, the change is at least 5-fold greater. Even more preferably, the change is at least 10-fold greater. Still more preferably, the change is at least 100 fold greater. Even still more preferably, the change is at least 500-fold greater. Ideally, modulation of each of the given systems by its respective ligand at a chosen concentration results in a measurable change in the magnitude of expression of the gene of that system and no measurable change in expression of all other systems operable in the cell, tissue, or organism. In such cases the multiple inducible gene regulation system is said to be "fully orthogonal".

Multiple Gene Expression Modulation System of The Invention

As described herein, Applicants' invention provides a multiple inducible gene regulation system that allows the simultaneous and quantitative regulation of two or more different genes in the same cell, tissue, or organism. Applicants have discovered that receptor based systems can be modified and combined to create a multiple inducible gene regulation system which comprises a plurality of individually operable gene regulation systems.

In a specific embodiment, the multiple inducible gene regulation system comprises a plurality of individually operable gene regulation systems wherein:
a) each individually operable gene regulation system comprises:
  i) one or more polynucleotides encoding a receptor complex comprising:
    A) a DNA binding domain;
    B) a ligand binding domain; and
    C) a transactivation domain;
  ii) a ligand;
  iii) a polynucleotide comprising:
    A) an exogenous or endogenous gene; and
    B) a response element;
  wherein:
    A) the exogenous or endogenous gene is under the control of the response element; and
    B) binding of the DNA binding domain to the response element in the presence or the absence of the ligand results in activation or suppression of the gene; and
b) each individually operable gene regulation system is orthogonal to the other individually operable gene regulation systems present in the multiple inducible gene regulation system.

In another embodiment, Applicants' invention also provides a multiple inducible gene regulation system which comprises a plurality of individually operable gene regulation systems wherein:
a) each individually operable gene regulation system comprises:
  i) one or more receptor complexes, each comprising:
    A) a DNA binding domain;
    B) a ligand binding domain; and
    C) a transactivation domain;
  ii) a ligand;
  iii) a polynucleotide comprising:
    A) an exogenous or endogenous gene; and
    B) a response element;
  wherein:
    A) the exogenous or endogenous gene is under the control of the response element; and
    B) binding of the DNA binding domain to the response element in the presence or the absence of the ligand results in activation or suppression of the gene; and
b) each individually operable gene regulation system is orthogonal to the other individually operable gene regulation systems present in the multiple inducible gene regulation system.

Applicants have found that nuclear receptors are preferred receptors for use in the multiple inducible gene expression systems of the present invention. Preferred nuclear receptors include Group H nuclear receptors. More preferred nuclear receptors include ecdysone receptors.

In nature, the EcR regulation system utilizes pulses of 20-hydroxyecdysone (20E), a steroid hormone, to regulate molting and other developmental processes in insects. 20E transduces its signal through a heterodimeric protein complex including ecdysone receptor (EcR) and ultraspiracle (USP). EcR controls expression of ecdysone-responsive genes by binding to ecdysone response elements (EcRE) present in their promoters. The EcR cDNA was first cloned from *D. melanogaster*. Both EcR and USP were found to be members of the nuclear receptor superfamily as they contain the characteristic domains: A/B (transactivation), C (DNA binding), D (hinge), and E (ligand binding). In total, twenty EcR sequences have been cloned from insects, crab and tick species (see infra). Comparison of deduced amino acid sequences from these cDNAs showed that the 66 amino acid DNA binding domain is well conserved among the EcRs whereas the A/B, D and F domains are not very well conserved. Critical residues in the ligand binding domain are well conserved. There is about 90% amino acid similarity in the ligand binding domains within a group of EcR sequences but this falls to 50-60% when compared between two groups.

Thus, preferred receptors for use in Applicants' multiple inducible gene expression systems include nuclear receptors; more preferred receptors include Group H nuclear receptors selected from the group consisting of ecdysone receptor, ubiquitous receptor (UR), Orphan receptor 1 (OR-1), steroid hormone nuclear receptor 1 (NER-1), RXR interacting protein-15 (RIP-15), liver x receptor β (LXRβ), steroid hormone receptor like protein (RLD-1), liver x receptor (LXR), liver x receptor α (LXRα), farnesoid x receptor (FXR), receptor interacting protein 14 (RIP-14), and farnesol receptor (HRR-1); even more preferred receptors include ecdysone receptors.

The present invention is useful for applications such as gene therapy, large scale production of proteins and antibodies, cell-based high throughput screening assays, orthogonal ligand screening assays, functional genomics, proteomics, metabolomics, biosensors, and regulation of traits in transgenic organisms, where control of gene expression levels is desirable. An advantage of Applicants' invention is that it provides a means to regulate expression of multiple genes and to tailor expression levels to suit the user's requirements.

In particular, Applicants describe herein a novel multiple inducible gene expression system comprising at least two individually operable gene expression systems. Each individually operable gene expression system comprises at least a first gene expression cassette comprising a response element, a promoter operatively linked to a polynucleotide or gene of interest to be expressed, the polynucleotide of gene of interest to be expressed. Induction of the first gene expression cassette may be accomplished using at least a second gene expression cassette.

In a specific embodiment, the second gene expression cassette comprises a polynucleotide encoding a polypeptide comprising a DNA binding domain that binds the response element of the first gene expression cassette, a transactivation domain that transactivates the promoter of the first gene expression cassette, and a ligand binding domain. This embodiment uses a "single switch"-based gene expression system to express the first gene expression cassette comprising the polynucleotide or gene of interest. A "single-switch"-based gene expression system is one in which the transactivation domain, DNA-binding domain and ligand binding domain are on one encoded polypeptide.

Alternatively, the gene expression modulation system may be a "dual switch"- or "two-hybrid"-based gene expression modulation system in which the transactivation domain and DNA-binding domain are located on two different encoded polypeptides. In this specific embodiment, induction of the first gene expression cassette may be accomplished using at least a second gene expression cassette and a third expression cassette. Preferably, the second gene expression cassette comprises a polynucleotide encoding a polypeptide comprising a DNA binding domain that binds the response element of the first gene expression cassette and a ligand binding domain; and the third gene expression cassette comprises a polynucleotide encoding a polypeptide comprising a transactivation domain that transactivates the promoter of the first gene expression cassette and a ligand binding domain.

In a preferred embodiment, the multiple inducible gene expression system of the invention comprises at least two gene expression modulation systems, wherein each operable gene expression modulation system comprises a) i) a first gene expression cassette comprising a polynucleotide that encodes a polypeptide comprising a transactivation domain, a DNA-binding domain that recognizes a response element associated with a gene whose expression is to be modulated; and a nuclear receptor ligand binding domain,
   ii) a ligand, and
   iii) a second gene expression cassette comprising: A) a response element recognized by the DNA-binding domain of the encoded polypeptide of the first gene expression cassette; B) a promoter that is activated by the transactivation domain of the encoded polypeptide of the first gene expression cassette; and C) a gene whose expression is to be modulated;
b) i) a first gene expression cassette comprising a polynucleotide that encodes a polypeptide comprising a transactivation domain, a DNA-binding domain that recognizes a response element associated with a gene whose expression is to be modulated; and a nuclear receptor ligand binding domain,
   ii) a second nuclear receptor ligand binding domain selected from the group consisting of a vertebrate retinoid X receptor ligand binding domain, an invertebrate retinoid X receptor ligand binding domain, an ultraspiracle protein ligand binding domain, and a chimeric ligand binding domain comprising two polypeptide fragments, wherein the first polypeptide fragment is from a vertebrate retinoid X receptor ligand binding domain, an invertebrate retinoid X receptor ligand binding domain, or an ultraspiracle protein ligand binding domain, and the second polypeptide fragment is from a different vertebrate retinoid X receptor ligand binding domain, invertebrate retinoid X receptor ligand binding domain, or ultraspiracle protein ligand binding domain,
   iii) a ligand, and
   iv) a second gene expression cassette comprising: A) a response element recognized by the DNA-binding domain of the encoded polypeptide of the first gene expression cassette; B) a promoter that is activated by the transactivation domain of the encoded polypeptide of the first gene expression cassette; and C) a gene whose expression is to be modulated; or
c) i) a first gene expression cassette comprising a polynucleotide that encodes a first polypeptide comprising a DNA-binding domain that recognizes a response element associated with a gene whose expression is to be modulated and a nuclear receptor ligand binding domain,
   ii) a second gene expression cassette comprising a polynucleotide that encodes a second polypeptide comprising a transactivation domain and a nuclear receptor ligand binding domain,
   iii) a ligand, and
   iv) a third gene expression cassette comprising: A) a response element recognized by the DNA-binding domain of the first polypeptide of the first gene expression cassette; B) a promoter that is activated by the transactivation domain of the second polypeptide of the second gene expression cassette; and C) a gene whose expression is to be modulated,
wherein one of the nuclear receptor ligand binding domains of c)i) or c)ii) is a Group H nuclear receptor ligand binding domain.

In another preferred embodiment, the multiple inducible gene expression system of the invention comprises at least two gene expression modulation systems, wherein each operable gene expression modulation system comprises a) i) a polypeptide comprising a transactivation domain, a DNA-binding domain that recognizes a response element associated with a gene whose expression is to be modulated; and a nuclear receptor ligand binding domain,
  ii) a ligand, and
  iii) a gene expression cassette comprising: A) a response element recognized by the DNA-binding domain of the polypeptide of a)i); B) a promoter that is activated by the transactivation domain of the polypeptide of a)i); and C) a gene whose expression is to be modulated;

b) i) a polypeptide comprising a transactivation domain, a DNA-binding domain that recognizes a response element associated with a gene whose expression is to be modulated; and a nuclear receptor ligand binding domain,
  ii) a second nuclear receptor ligand binding domain selected from the group consisting of a vertebrate retinoid X receptor ligand binding domain, an invertebrate retinoid X receptor ligand binding domain, an ultraspiracle protein ligand binding domain, and a chimeric ligand binding domain comprising two polypeptide fragments, wherein the first polypeptide fragment is from a vertebrate retinoid X receptor ligand binding domain, an invertebrate retinoid X receptor ligand binding domain, or an ultraspiracle protein ligand binding domain, and the second polypeptide fragment is from a different vertebrate retinoid X receptor ligand binding domain, invertebrate retinoid X receptor ligand binding domain, or ultraspiracle protein ligand binding domain,
  iii) a ligand, and
  iv) a gene expression cassette comprising: A) a response element recognized by the DNA-binding domain of the polypeptide of b)i); B) a promoter that is activated by the transactivation domain of the polypeptide of b)i); and C) a gene whose expression is to be modulated; or c) i) a first polypeptide comprising a DNA-binding domain that recognizes a response element associated with a gene whose expression is to be modulated and a nuclear receptor ligand binding domain,
  ii) a second polypeptide comprising a transactivation domain and a nuclear receptor ligand binding domain,
  iii) a ligand, and
  iv) a gene expression cassette comprising: A) a response element recognized by the DNA-binding domain of the first polypeptide of c)i); B) a promoter that is activated by the transactivation domain of the second polypeptide of c)ii); and C) a gene whose expression is to be modulated, wherein one of the nuclear receptor ligand binding domains of c)i) or c)ii) is a Group H nuclear receptor ligand binding domain.

In a preferred embodiment, when the gene expression modulation system comprises C), the first polypeptide is substantially free of a transactivation domain and the second polypeptide is substantially free of a DNA binding domain. For purposes of the invention, "substantially free" means that the protein in question does not contain a sufficient sequence of the domain in question to provide activation or binding activity. Wherein when only one nuclear receptor ligand binding domain is a Group H ligand binding domain, the other nuclear receptor ligand binding domain may be from any other nuclear receptor that forms a dimer with the Group H ligand binding domain. For example, when the Group H nuclear receptor ligand binding domain is an ecdysone receptor ligand binding domain, the other nuclear receptor ligand binding domain ("partner") may be from an ecdysone receptor, a vertebrate retinoid X receptor (RXR), an invertebrate RXR, an ultraspiracle protein (USP), or a chimeric nuclear receptor comprising at least two different nuclear receptor ligand binding domain polypeptide fragments selected from the group consisting of a vertebrate RXR, an invertebrate RXR, and a USP (see co-pending applications PCT/US01/09050, U.S. Ser. No. 60/294,814, and U.S. Ser. No. 60/294,819, incorporated herein by reference in their entirety). The "partner" nuclear receptor ligand binding domain may further comprise a truncation mutation, a deletion mutation, a substitution mutation, or another modification.

Preferably, the vertebrate RXR ligand binding domain is from a human *Homo sapiens*, mouse *Mus musculus*, rat *Rattus norvegicus*, chicken *Gallus gallus*, pig *Sus scrofa domestica*, frog *Xenopus laevis*, zebrafish *Danio rerio*, tunicate *Polyandrocarpa misakiensis*, or jellyfish *Tripedalia cysophora* RXR.

Preferably, the invertebrate RXR ligand binding domain is from a locust *Locusta migratoria* ultraspiracle polypeptide ("LmUSP"), an ixodid tick *Amblyomma americanum* RXR homolog 1 ("AmaRXR1"), a ixodid tick *Amblyomma americanum* RXR homolog 2 ("AmaRXR2"), a fiddler crab *Celuca pugilator* RXR homolog ("CpRXR"), a beetle *Tenebrio molitor* RXR homolog ("TmRXR"), a honeybee *Apis mellifera* RXR homolog ("AmRXR"), an aphid *Myzus persicae* RXR homolog ("MpRXR"), or a non-Dipteran/non-Lepidopteran RXR homolog. See co-pending U.S. provisional patent application 60/294,814 filed May 31, 2001, incorporated herein by reference in its entirety.

Preferably, the chimeric RXR ligand binding domain comprises at least two polypeptide fragments selected from the group consisting of a vertebrate species RXR polypeptide fragment, an invertebrate species RXR polypeptide fragment, and a non-Dipteran/non-Lepidopteran invertebrate species RXR homolog polypeptide fragment. A chimeric RXR ligand binding domain for use in the present invention may comprise at least two different species RXR polypeptide fragments, or when the species is the same, the two or more polypeptide fragments may be from two or more different isoforms of the species RXR polypeptide fragment. See co-pending U.S. provisional patent application 60/294,819 filed May 31, 2001, incorporated herein by reference in its entirety.

In a specific embodiment, the gene whose expression is to be modulated is a homologous gene with respect to the host cell. In another specific embodiment, the gene whose expression is to be modulated is a heterologous gene with respect to the host cell.

Preferably, one or more of the receptor domains is varied producing a hybrid gene switch. Typically, one or more of the three domains, DBD, LBD, and transactivation domain, may be chosen from a source different than the source of the other domains so that the hybrid genes and the resulting hybrid proteins are optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski, et al. (1988) Nature, 335:563-564) or LexA protein from *Escherichia coli* (see Brent and Ptashne (1985), Cell, 43:729-736), or synthetic response elements specific for targeted interactions with proteins designed, modified, and selected for such specific interactions (see, for example, Kim, et al. (1997), *Proc. Natl. Acad. Sci., USA,* 94:3616-3620) to accommodate hybrid receptors. Another advantage of two-hybrid systems is that they allow choice of a promoter used to drive the gene expression according to a desired end result. Such double control can be particularly important in areas of gene therapy, especially when cytotoxic proteins are produced, because both the timing of expression as well as the cells wherein expression occurs can be controlled. When genes, operably linked to a suitable promoter, are introduced into the cells of the subject, expression of the exogenous genes is controlled by the presence of the system of this invention. Promoters may be constitutively or inducibly regulated or may be tissue-specific (that is, expressed only in a particular type of cells) or specific to certain developmental stages of the organism.

An ecdysone receptor-based gene expression modulation system of the present invention may be either heterodimeric and homodimeric. A functional EcR complex generally refers to a heterodimeric protein complex consisting of two members of the steroid receptor family, an ecdysone receptor protein obtained from various insects, and an ultraspiracle (USP) protein or the vertebrate homolog of USP, retinoid X receptor protein (see Yao, et al. (1993) Nature 366, 476-479; Yao, et al., (1992) Cell 71, 63-72). However, the complex may also be a homodimer as detailed below. The functional ecdysteroid receptor complex may also include additional protein(s) such as immunophilins. Additional members of the steroid receptor family of proteins, known as transcriptional factors (such as DHR38 or betaFTZ-1), may also be ligand dependent or independent partners for EcR, USP, and/or RXR. Additionally, other cofactors may be required such as proteins generally known as coactivators (also termed adapters or mediators). These proteins do not bind sequence-specifically to DNA and are not involved in basal transcription. They may exert their effect on transcription activation through various mechanisms, including stimulation of DNA-binding of activators, by affecting chromatin structure, or by mediating activator-initiation complex interactions. Examples of such coactivators include RIP140, TIF1, RAP46/Bag-1, ARA70, SRC-1/NCoA-1, TIF2/GRIP/NCoA-2, ACTR/AIB1/RAC3/pCIP as well as the promiscuous coactivator C response element B binding protein, CBP/p300 (for review see Glass et al., Curr. Opin. Cell Biol. 9:222-232, 1997). Also, protein cofactors generally known as corepressors (also known as repressors, silencers, or silencing mediators) may be required to effectively inhibit transcriptional activation in the absence of ligand. These corepressors may interact with the unliganded ecdysone receptor to silence the activity at the response element. Current evidence suggests that the binding of ligand changes the conformation of the receptor, which results in release of the corepressor and recruitment of the above described coactivators, thereby abolishing their silencing activity. Examples of corepressors include N-CoR and SMRT (for review, see Horwitz et al. Mol Endocrinol. 10: 1167-1177, 1996). These cofactors may either be endogenous within the cell or organism, or may be added exogenously as transgenes to be expressed in either a regulated or unregulated fashion. Homodimer complexes of the ecdysone receptor protein, USP, or RXR may also be functional under some circumstances.

The ecdysone receptor complex typically includes proteins that are members of the nuclear receptor superfamily wherein all members are generally characterized by the presence of an amino-terminal transactivation domain, a DNA binding domain ("DBD"), and a ligand binding domain ("LBD") separated from the DBD by a hinge region. As used herein, the term "DNA binding domain" comprises a minimal polypeptide sequence of a DNA binding protein, up to the entire length of a DNA binding protein, so long as the DNA binding domain functions to associate with a particular response element. Members of the nuclear receptor superfamily are also characterized by the presence of four or five domains: A/B, C, D, E, and in some members F (see U.S. Pat. No. 4,981,784 and Evans, *Science* 240:889-895 (1988)). The "A/B" domain corresponds to the transactivation domain, "C" corresponds to the DNA binding domain, "D" corresponds to the hinge region, and "E" corresponds to the ligand binding domain. Some members of the family may also have another transactivation domain on the carboxy-terminal side of the LBD corresponding to "F".

The DBD is characterized by the presence of two cysteine zinc fingers between which are two amino acid motifs, the P-box and the D-box, which confer specificity for ecdysone response elements. These domains may be naturally occurring; modified by deletion, insertion, or mutation; synthetic; chimeras of different domains of heterologous receptor proteins; or a combination thereof. This receptor, like a subset of the steroid receptor family, also possesses less well defined regions responsible for heterodimerization properties. Because the domains of EcR, USP, and RXR are modular in nature, the LBD, DBD, and transactivation domains may be interchanged.

Gene Expression Cassettes

The novel multiple inducible gene expression system of the invention comprises gene expression cassettes that are capable of being expressed in a host cell, wherein the gene expression cassettes each comprise a polynucleotide that encodes a polypeptide of interest, either as a "switch" polypeptide to induce expression of a polypeptide or gene of interest, or the polypeptide or gene of interest desired to be expressed by the multiple inducible gene expression system of the invention. Thus, Applicants' invention also provides gene expression cassettes for use in the multiple inducible gene expression system of the invention.

In a specific embodiment, the gene expression cassette that is capable of being expressed in a host cell comprises a polynucleotide that encodes a polypeptide selected from the group consisting of a) a polypeptide comprising a transactivation domain, a DNA-binding domain, and a nuclear receptor ligand binding domain; b) a polypeptide comprising a DNA-binding domain and a nuclear receptor ligand binding domain; and c) a polypeptide comprising a transactivation domain and a nuclear receptor ligand binding domain.

In another specific embodiment, the present invention provides a gene expression cassette that is capable of being expressed in a host cell, wherein the gene expression cassette comprises a polynucleotide that encodes a hybrid polypeptide selected from the group consisting of a) a hybrid polypeptide comprising a transactivation domain, a DNA-binding domain, and a nuclear receptor ligand binding domain; b) a hybrid polypeptide comprising a DNA-binding domain and a nuclear receptor ligand binding domain; and c) a hybrid polypeptide comprising a transactivation domain and a nuclear receptor ligand binding domain. A hybrid polypeptide according to the invention comprises at least two polypeptide fragments, wherein each polypeptide fragment is from a different source, i.e., a different polypeptide, a different nuclear receptor, a different species, etc. The hybrid polypeptide according to the invention may comprise at least two polypeptide domains, wherein each polypeptide domain is from a different source.

In a specific embodiment, the nuclear receptor ligand binding domain is a Group H nuclear receptor selected from the group consisting of an ecdysone receptor, a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor 1, a liver X receptor α, a farnesoid X receptor, a receptor interacting protein 14, and a farnesol receptor. In a preferred embodiment, the nuclear receptor ligand binding domain is from an ecdysone receptor.

Thus, the present invention also provides a gene expression cassette comprising a polynucleotide that encodes a polypeptide selected from the group consisting of a) a polypeptide comprising a transactivation domain, a DNA-binding domain, and an ecdysone receptor ligand binding domain; b) a polypeptide comprising a DNA-binding domain and an ecdysone receptor ligand binding domain; and c) a polypeptide comprising a transactivation domain and an ecdysone receptor ligand binding domain. Preferably, the gene expression cassette comprises a polynucleotide that encodes a hybrid polypeptide selected from the group consisting of a) a hybrid polypeptide comprising a transactivation domain, a DNA-binding domain, and an ecdysone receptor ligand binding domain; b) a hybrid polypeptide comprising a DNA-binding domain and an ecdysone receptor ligand binding domain; and c) a hybrid polypeptide comprising a transactivation domain and an ecdysone receptor ligand binding domain; wherein the encoded hybrid polypeptide comprises at least two polypeptide fragments, wherein each polypeptide fragment is from a different source.

The ecdysone receptor (EcR) ligand binding domain (LBD) may be from an invertebrate EcR selected from the group consisting of a Lepidopteran EcR, a Dipteran EcR, an Arthropod EcR, an Orthopteran EcR, a Homopteran EcR and a Hemipteran EcR. Preferably, the EcR ligand binding domain for use in the present invention is from a spruce budworm *Choristoneura fumiferana* EcR ("CfEcR"; Kothapalli et al., 1995 Dev Genet. 17:319-30), a yellow meal worm *Tenebrio molitor* EcR ("TmEcR"; Mouillet et al., 1997, Eur. J. biochem. 248:856-863), a tobacco hormworm *Manduca sexta* EcR ("MsEcR"; Fujiwara et al., 1995, Insect Biochem. Molec. Biol. 25, 845-856), a tobacco budworm *Heliothies virescens* EcR ("HvEcR"; Martinez et al., 1999, Insect Biochem Mol Biol. 29:915-30), a golmidge *Chironomus tentans* EcR ("CtEcR"; Imhof et al., 1993, *Insect Biochem. Molec. Biol.* 23, 115-124), a silkworm *Bombyx mori* EcR ("BmEcR"; Swevers et al., 1995, Insect Biochem. Molec. Biol. 25, 857-866), a squinting bush brown *Bicyclus anynana* EcR ("BanEcR"), a buckeye *Junonia coenia* EcR ("JcEcR"), a fruit fly *Drosophila melanogaster* EcR ("DmEcR"; Koelle et al., 1991, Cell 67, 59-77), a yellow fever mosquito *Aedes aegypti* EcR ("AaEcR"; Cho et al., 1995, Insect Biochem. Molec. Biol. 25, 19-27), a blowfly *Lucilia capitata* ("LcEcR"), a sheep blowfly *Lucilia cuprina* EcR ("LucEcR"; Hannan and Hill, 1997, Insect Biochem. Molec. Biol. 27, 479-488), a blowfly *Calliphora vicinia* EcR ("CvEcR"), a Mediterranean fruit fly *Ceratitis capitata* EcR ("CcEcR"; Verras et al., 1999, *Eur J Biochem.* 265:798-808), a locust *Locusta migratoria* EcR ("LmEcR"; Saleh et al., 1998, *Mol Cell Endocrinol.* 143:91-9), an aphid *Myzus persicae* EcR ("MpEcR"; International Patent Application Publication WO99/36520), a fiddler crab *Celuca pugilator* EcR ("CpEcR"; Chung et al., 1998, *Mol Cell Endocrinol* 139:209-27), an ixodid tick *Amblyomma americanum* EcR ("AmaEcR"; Guo et al., 1997, Insect Biochem. Molec. Biol. 27, 945-962), a white fly *Bamecia argentifoli* ("BaEcR"), US provisional patent application filed Sep. 26, 2001, incorporated herein by reference in its entirety), or a green leafhopper *Nephotetix cincticeps* ("NcEcR"; Palli, US provisional patent application filed Sep. 26, 2001, incorporated herein by reference in its entirety). More preferably, the LBD is from a CfEcR, a DmEcR, or an NcEcR.

The DNA binding domain can be any DNA binding domain with a known response element, including synthetic and chimeric DNA binding domains, or analogs, combinations, or modifications thereof. Preferably, the DBD is a GAL4 DBD, a LexA DBD, a transcription factor DBD, a Group H nuclear receptor member DBD, a steroid/thyroid hormone nuclear receptor superfamily member DBD, or a bacterial LacZ DBD. More preferably, the DBD is an EcR DBD, a GAL4 DBD, or a LexA DBD.

The transactivation domain (abbreviated "AD" or "TA") may be any Group H nuclear receptor member AD, steroid/thyroid hormone nuclear receptor AD, synthetic or chimeric AD, polyglutamine AD, basic or acidic amino acid AD, a VP 16 AD, a GAL4 AD, an NF-κB AD, a BP64 AD, a B42 acidic activation domain (B42AD), a p65 transactivation domain (p65AD), or an analog, combination, or modification thereof. In a specific embodiment, the AD is a synthetic or chimeric AD, or is obtained from an EcR, a glucocorticoid receptor, VP 16, GAL4, NF-kB, or B42 acidic activation domain AD. Preferably, the AD is an EcR AD, a VP16 AD, a B42 AD, or a p65 AD.

The present invention also provides a gene expression cassette comprising: i) a response element comprising a domain recognized by a polypeptide comprising a DNA binding domain; ii) a promoter that is activated by a polypeptide comprising a transactivation domain; and iii) a gene whose expression is to be modulated.

The response element ("RE") may be any response element with a known DNA binding domain, or an analog, combination, or modification thereof. A single RE may be employed or multiple REs, either multiple copies of the same RE or two or more different REs, may be used in the present invention. In a specific embodiment, the RE is an RE from GAL4 ("GAL4RE"), LexA, a Group H nuclear receptor RE, a steroid/thyroid hormone nuclear receptor RE, or a synthetic RE that recognizes a synthetic DNA binding domain. Preferably, the RE is an ecdysone response element (EcRE), a GAL4RE, or a LexA RE (operon, "op").

A steroid/thyroid hormone nuclear receptor DNA binding domain, activation domain or response element according to the invention may be obtained from a steroid/thyroid hormone nuclear receptor selected from the group consisting of thyroid hormone receptor α (TRα), thyroid receptor 1 (c-erbA-1), thyroid hormone receptor α (THRA), thyroid hormone receptor β (TRβ), thyrpid hormone receptor β (THRB), retinoic acid receptor α (RARα), retinoic acid receptor β (RARβ), hepatoma (HAP), retinoic acid receptor γ (RARγ), retinoic acid recetor gamma-like (RARD), peroxisome proliferator-activated receptor α (PPARα), peroxisome proliferator-activated receptor β (PPARβ), peroxisome proliferator-activator related receptor (NUC-1), peroxisome proliferator-activated receptor δ (PPARδ), peroxisome proliferator-activator related receptor (FFAR), peroxisome proliferator-activated receptor γ (PPARγ), orphan receptor encoded by non-encoding strand of thyroid hormone receptor α (REVERBα), v-erb A related receptor (EAR-1), v-erb related receptor (EAR-1A), γ), orphan receptor encoded by non-encoding strand of thyroid hormone receptor β (REVERβ), v-erb related receptor (EAR-1β), orphan nuclear recptor BD73 (BD73), rev-erbA-related receptor (RVR), zinc finger protein 126 (HZF2), ecdysone-inducible protein E75 (E75), ecdysone-inducible protein E78 (E78), Drosophila receptor 78 (DR-78), retinoid-related orphan receptor α (RORα), retinoid x receptor α (RZRα), retinoid related orphan receptor β (RORβ), retinoid Z receptor β (RZRβ), retinoid-related orphan receptor γ (RORγ), retinoid Z receptor γ (RZRγ), retinoid-related orphan receptor (TOR), hormone receptor 3 (HR-3), Drosophila hormone receptor 3 (DHR-3), myohemerythin (MHR-3), growth hormone receptor 3 (GHR-3), C. elegans nuclear receptor 3 (CNR-3), C. elegans hormone receptor 3 (CHR-3), C. elegans nuclear receptor 14 (CNR-14), ecdysone receptor (ECR), ubiquitous receptor (UR), orphan nuclear receptor (OR-1), NER-1, receptor-interacting protein 15 (RIP-15), liver X receptor β (LXRβ), steroid hormone receptor like protein (RLD-1), liver X receptor (LXR), liver X receptor α (LXRα), farnesoid X receptor (FXR), receptor-interacting protein 14 (RIP-14), HRR-1, vitamin D receptor (VDR), orphan nuclear receptor (ONR-1), pregnane X receptor (PXR), steroid and xenobiotic receptor (SXR), benzoate X receptor (BXR), nuclear receptor (MB-67), constitutive androstane receptor 1 (CAR-1), constitutive androstane receptor α (CARα), constitutive androstane receptor 2 (CAR-2), constitutive androstane receptor β (CARβ), Drosophila hormone receptor 96 (DHR-96), nuclear hormone receptor 1 (NHR-1), hepatocyte nuclear factor 4 (HNF-4), hepatocyte nuclear factor 4G (HNF-4G), hepatocyte nuclear factor 4B (HNF-4B), DHNF-4, hepatocyte nuclear factor 4D (HNF-4D), retinoid X receptor α (RXRα), retinoid X receptor β (RXRβ), H-2 region II binding protein (H-2RIIBP), nuclear receptor co-regulator-1 (RCoR-1), retinoid X receptor γ (RXRγ), Ultraspiracle (USP), 2C1, chorion factor 1 (CF-1), testicular receptor (TR-2), testicular receptor (TR2-11), TR4, TAK-1, Drosophila hormone receptor (DHR78), Tailless (TLL), tailless homolog (TLX), XTLL, chicken ovalbumin upstream promoter transcription factor I (COUP-TFI), chicken ovalbumin upstream promoter transcription factor A (COUP-TFA), EAR-3, SVP-44, chicken ovalbumin upstream promoter transcription factor II (COUP-TFII), chicken ovalbumin upstream promoter transcription factor B (COUP-TFB), ARP-1, SVP-40, SVP, chicken ovalbumin upstream promoter transcription factor III (COUP-TFIII), chicken ovalbumin upstream promoter transcription factor G (COUP-TFG), SVP-46, EAR-2, estrogen receptor α (ERα), estrogen receptor β (ERβ), estrogen related receptor 1 (ERR1), estrogen related receptor α (ERRα), estrogen related receptor 2 (ERR2), estrogen related receptor β (ERRβ), glucocorticoid receptor (GR), mineralocorticoid receptor (MR), progesterone receptor (PR), androgen receptor (AR), nerve growth factor induced gene B (NGFI-B), nuclear receptor similar to Nur-77 (TRS), N10, Orphan receptor (NIR-77), Human early response gene (NAK-1), Nurr related factor 1 (NURR-1), a human immediate-early response gene (NOT), regenerating liver nuclear receptor 1 (RNR-1), hematopoietic zinc finger 3 (HZF-3), Nur rekated protein-1 (TINOR), Nuclear orphan receptor 1 (NOR-1), NOR1 related receptor (MINOR), Drosophila hormone receptor 38 (DHR-38), C. elegans nuclear receptor 8 (CNR-8), C48D5, steroidogenic factor 1 (SF1), endozepine-like peptide (ELP), fushi tarazu factor 1 (FTZ-F1), adrenal 4 binding protein (AD4BP), liver receptor homolog (LRH-1), Ftz-F1-related orphan receptor A (xFFrA), Ftz-F1-related orphan receptor B (xFFrB), nuclear receptor related to LRH-1 (FFLR), nuclear receptor related to LRH-1 (PHR), fetoprotein transcriptin factor (FTF), germ cell nuclear factor (GC-NFM), retinoid receptor-related testis-associated receptor (RTR), knirps (KNI), knirps related (KNRL), Embryonic gonad (EGON), Drosophila gene for ligand dependent nuclear receptor (EAGLE), nuclear receptor similar to trithorax (ODR7), Trithorax, dosage sensitive sex reversal adrenal hypoplasia congenita critical region chromosome X gene (DAX-1), adrenal hypoplasia congenita and hypogonadotropic hypogonadism (AHCH), and short heterodimer partner (SHP).

For purposes of this invention, nuclear receptors, Group H nuclear receptors, EcR, USP, and RXR also include synthetic and chimeric nuclear receptors, Group H nuclear receptors, ecdysone receptors, EcR, USP, RXR, and their homologs.

Genes of interest for use in Applicants' gene expression cassettes may be endogenous genes or heterologous genes. Nucleic acid or amino acid sequence information for a desired gene or protein can be located in one of many public access databases, for example, GENBANK, EMBL, Swiss-Prot, and PIR, or in many biology related journal publications. Thus, those skilled in the art have access to nucleic acid sequence information for virtually all known genes. Such information can then be used to construct the desired constructs for the insertion of the gene of interest within the gene expression cassettes used in Applicants' methods described herein.

Examples of genes of interest for use in Applicants' gene expression cassettes include, but are not limited to: genes encoding therapeutically desirable polypeptides or products that may be used to treat a condition, a disease, a disorder, a dysfunction, a genetic defect, such as monoclonal antibodies, enzymes, proteases, cytokines, interferons, insulin, erthropoietin, clotting factors, other blood factors or components, viral vectors for gene therapy, virus for vaccines, targets for drug discovery, functional genomics, and proteomics analyses and applications, and the like.

The following procedures are used to prepare the multiple gene regulation systems of this invention:

Multiple gene regulation systems require initial development of the regulation system ligands, which are used to screen novel ligand binding domain (LBDs). Then unique DNA binding domains (DBDs) are created from which corresponding high affinity DNA response elements (REs) are isolated. Finally, a unique collection of nuclear receptors (NRs) are created by fusing the novel LBDs and DBDs to well-characterized transcriptional activation domains (ADs).

To develop a set of non-cross-interactive ("fully orthogonal") ligand/receptor pairs the lead structures for both ligand and receptor are maximally structurally diverse. For ecdysone-based receptors, two chemotypes are ideal for use as ligands: the natural ecdysteroids, such as, for example, 20-hydroxyecdsone, and the diacylhydrazines.

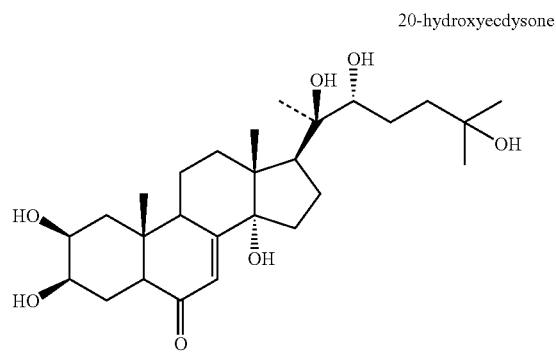

20-hydroxyecdysone

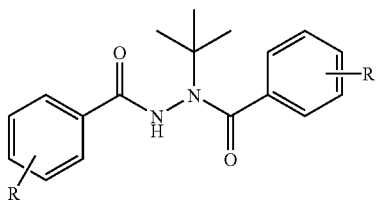

diacylhydrazine

Natural ecdysteroids are potent (Kds as low as ca. 1 nM) but appear to be quite cross-interactive across insect species, based on available data in whole insect and cell-based assays. The diacylhydrazines (Kds as low as ca. 0.5 nM), for the most part, also appear to be cross-interactive for the EcRs on which they are active at all (see Dhadialla et al. (1998) Annu Rev Entomol, 43:545-69). An orthogonal ligand/receptor set does not exist within these two structural families. To achieve the goal of a multiple, orthogonal gene regulation system, ligand identification requires both pharmacophore matching for the specified receptor as well as pharmacophore mismatching for the non-interacting receptors. We have discovered just such an orthogonal system.

Acceptable ligands are any which modulate expression of the gene when binding of the DBD to the response element in the presence of the ligand results in activation or suppression of expression of one of the genes in the multiple gene regulation system and which do not activate or suppress the other genes of the multiple regulation system, that is, the system is orthogonal. Preferred ligands include the naturally occurring hormones ponasterone and muristerone A, their derivatives and/or analogs as well as N,N'-diacylhydrazines such as those disclosed in U.S. Pat. Nos. 6,013,836, 5,117,057, 5,530,021, and 5,378,726; dibenzoylalkyl cyanohydrazines such as those disclosed in European Application No. 461,809; N-alkyl-N,N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; each of which is incorporated herein by reference and other similar materials including 3,5-di-tert-butyl-4-hydroxy-N-isobutyl-benzamide, 8-O-acetylharpagide, ecdysone, 20-hydroxyecdysone, ponasterone A, muristerone A, oxysterols, 22(R) hydroxycholesterol, 24(S) hydroxycholesterol, 25-epoxycholesterol, T0901317, 5-alpha-6-alpha-epoxycholesterol-3-sulfate (ECHS), 7-keto-cholesterol-3-sulfate, farnesol, bile acids, 1,1-biphosphonate esters, Juvenile hormone III, and the like.

Since a multiple gene regulation system requires discreet ligands that will not cross-react among themselves or with other receptors within the cell, but are specific for and induce only a specific receptor, several strategies are used to define the appropriate ligands for each multiple gene regulation system combination.

Ligand complementation starts from a known highly active ligand and proceeds in one of three ways:

1) Stepwise change of individual pharmacophore (i.e., active site) element (PE) identity on the ligand, wherein a ligand pharmacophore is hypothesized, an element within the pharmacophore is dramatically altered and a mutant receptor library is queried for a complementary alteration. Once a successful mutant/ligand combination is identified, a protein modeling-ligand design iterative sequence is utilized to optimize the ligand/receptor interaction, either maximizing the response or minimizing the response (in the case where it is desirable to suppress gene expression rather than induce expression).

2) Addition of a new ligand "variable domain", wherein the pharmacophore and the complementary binding locus remain more or less constant. An additional group, non-essential but potentially detrimental to binding to natural receptors is attached to the core ligand. The size and nature of this group permits variegated modification and functionalization. As before, the mutant receptor library is then queried.

3) Wholesale removal of a cluster of ligand pharmacophore elements and replacement with a new PE map (akin to the concept of chimerical structures) wherein one retains roughly half of the known pharmacophore, and replaces the missing pharmacophore cluster with diverse entities. These new molecular fragments provide alternative PE patterns or else partially (but not entirely) replicate the original pattern. Mutant receptor libraries, members of which bear residue modifications at PE binding loci and/or cavity shape modification, are subsequently queried for complementarity to the newly perturbed pharmacophore.

From the ligand point of view, the procedure is as follows:
1. Define a set of diversely-modified ligands based on incremental PE changes, addition of a new ligand "variable domain" and wholesale PE cluster replacement. The starting ligand templates include diacylhydrazines and the natural ecdysteroids.
2. Prepare a set of receptors wherein the receptor LBDs are naturally occurring; modified by deletion, insertion, or mutation; synthetic; chimeras of different domains of heterologous receptor proteins; or a combination thereof. Modifications can occur via DNA shuffling, ITCHY or mutagenesis from a plurality of natural receptors. LBD mutations should probe regions of the binding pocket and ideally sample residues of ± charge, of lipophilic character and that may act as H-bond donors/acceptors from suspected binding points.
3. Optionally, introduce mutant receptors into cells.
4. Query the receptor set with ligand set for gene modulation and/or binding, wherein both gene modulation and binding queries may be performed either in vivo (in cells in which the mutant receptors have been introduced) or in vitro. Preferably the gene modulation query is performed in vivo in cells and the binding query is performed in vitro.
5. Data analysis—tabulate magnitude of induction/binding as a function of receptor and ligand. Examine the grid for orthogonality (receptor/ligand combinations which are mutually non-productive as gene regulation systems).
6. Optimize—Repeat steps 1-5 with more focused ligand modification and site-specific LBD-mutations based on the structure/activity results from first round and protein homology modeling information.

Ligands appropriate for these approaches should; 1) be readily synthetically accessible, 2) show potential for acceptable pharmacokinetics as drugs, and 3) lend themselves to structural modification. Both the ecdysteroids and diacylhydrazines qualify, although steroid modification is more synthetically demanding and, in order to function optimally, should eliminate chemical functionality that lends itself to metabolism.

As used herein, the term "set" means one or more. Preferably, however, a "set" or "library" includes two or more members. Typically, a set will include many more members than the total number of individually operable gene regulation systems in the multiple inducible gene regulation system.

Each individual system comprising the multiple gene regulation systems within a cell requires an appropriate receptor. For purposes of this invention, the term "cell" includes viruses. Although many receptors are applicable to the system of this invention; nuclear receptors are preferred. EcR-based gene regulation systems are ideal for use in the present invention because each regulation system offers very tight regulation of gene expression and there is sufficient variability in the EcR family to make possible the generation of multiple novel EcR receptors. A number of technologies are known in the art to introduce mutations into a DNA sequence including site-directed mutagenesis, error-prone PCR, use of the AL-1 Red mutator strain, DNA shuffling (see Chang, C. C., et al (1999) *Nat Biotechnol,* 17(8), 793-7 and Stemmer, W. P. (1994) *Proc Natl Acad Sci USA,* 91(22), 10747-51), and Incremental Truncation for the Creation of Hybrid Enzymes, also known as ITCHY (see Michnick, S. W. and Arnold, F. H. (1999) *Nat Biotechnol,* 17(12), 1159-60 and Ostermeier, M., et al (1999) *Nat Biotechnol,* 17(12), 1205-9).

The EcR LBD from *Choristeneuria fumiferana* (CfEcR) is an ideal candidate for mutagenesis because it has shown high ligand binding affinity with certain diacylhydrazines. However, other ecdysone receptors, as well as other nuclear receptors may be mutated for use within the system of the present invention. Random mutagenesis by site directed mutagenesis, error prone PCR and by using mutator strain *Epicurian coli*, XL1-Red will produce a number of random mutations in the CfEcR LBD. The XL-1 Red mutator strain is engineered to be deficient in three genes involved in DNA repair, mutS, mutD and mutT. Transformation of a plasmid into the strain results in the generation of randomly integrated mutations throughout the sequence because the strain has a 5,000 fold higher rate of mutation. The resulting polynucleotides encoding the mutated LBDs are then cloned into appropriate vectors and libraries are created. The libraries are subsequently screened using the methods that follow. Ecdysone receptors comprising truncation mutations and substitution mutations that affect ligand binding, specificity and/or sensitivity have recently been obtained (see co-pending International Patent Application No. PCT/US01/19050 and US provisional application entitled "Novel Substitution Mutant Receptors and Their Use in a Nuclear Receptor-Based Inducible Gene Expression System" of Palli et al., Serial No. not yet assigned, filed Aug. 21, 2001, incorporated herein by reference in their entirety).

Substitution mutations may be made by any technique for mutagenesis known in the art, including but not limited to, in vitro site-directed mutagenesis (Hutchinson, C., et al., 1978, J. Biol. Chem. 253:6551; Zoller and Smith, 1984, DNA 3:479-488; Oliphant et al., 1986, Gene 44:177; Hutchinson et al., 1986, Proc. Natl. Acad. Sci. U.S.A. 83:710), use of TAB® linkers (Pharmacia), restriction endonuclease digestion/fragment deletion and substitution, PCR-mediated/oligonucleotide-directed mutagenesis, and the like. PCR-based techniques are preferred for site-directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61-70).

DNA shuffling is a technique that takes advantage of the sequence homology a family of genes shares. In this process, the family of genes is cloned into a common vector and PCR amplified using a set of primers specific to vector sequences flanking the insert. In this manner, all of the amplified genes will share the same 5' and 3' sequences. The PCR amplified gene products are then treated with DNaseI and the resulting fragments in the 10-60 base pair ("bp") size range are gel purified. Those fragments are then used in a PCR reaction that does not contain oligonucleotides as primers. In this fashion, priming for Taq DNA polymerase extension of template comes from the annealing of homologous regions in the family of genes. Following this round of DNA shuffling, the process can be successively repeated to generate a saturated library of shuffled sequences. At the completion of the shuffling, a PCR amplification is performed with the primers that were used to amplify the cloned sequences from the vector. In this manner, a library of shuffled genes is amplified whose members are typically of the same size as their parental genes. The library is then cloned and assayed for the desired phenotype (see Stemmer, 1994, above). Again, nuclear receptors and EcR in particular are a good choice for this process in that the nuclear receptor superfamily, of which EcR is a member, contains over 300 recognized members from vertebrates, arthropods and nematodes.

As an alternative to developing multiple, Group H nuclear-based gene regulation systems simply by utilizing the array of wild type Group H nuclear receptors currently available from different species and engineering a unique ligand for each of them, one may also engineer novel Group H nuclear receptor LBDs that still conform to the basic receptor/nuclear receptor/Group H nuclear, preferably EcR, architecture (see co-pending US provisional patent application, serial number not yet assigned entitled "Novel Substitution Mutant Receptors And Their Use In A Nuclear Receptor-Based Inducible Gene Expression System", Inventors: Palli et al., filed Aug. 21, 2001, that describes Group H nuclear receptor ligand binding domainds comprising substitution mutations that modify ligand binding domain ligand sensitivity, specificity or magnitude of transactivation; incorporated herein by reference in its entirety). In order to accomplish this, DNA sequences from a multitude of the most divergent sequences are shuffled. The advantage lies in the fact that there is significant nucleic acid sequence homology among many known and cloned receptors. This provides a greater chance to generate a library of receptors containing novel LBDs.

An important aspect of this invention is that by utilizing human nuclear receptors in this process, multiple gene regulation systems with human gene therapy applications can be developed. In addition, DNA shuffling may utilize human nuclear receptor sequences to generate novel DBDs. As with EcR shuffling to obtain novel LBDs, there are advantages and disadvantages to shuffling different human nuclear receptors together to obtain novel DBDs. The advantages are two-fold. First, utilizing human sequences greatly reduces the chances for antigenicity of the novel receptors in human gene therapy applications. Second, a greater probability exists in generating novel DBDs by shuffling different human nuclear hormone receptors from within the superfamily than by shuffling EcRs from different species given the greater C domain sequence diversity. However, in order for DNA shuffling to be successful, a minimal amount of homology must exist.

Nuclear receptors bind DNA either as heterodimers with RXR, as homodimers or as monomers. The dimerization domain of the nuclear receptor superfamily is bipartite; it is divided between the C and E domains of the receptor. This invention only utilizes the C domain of shuffled human nuclear receptors. Therefore, it is logical to choose to shuffle those human receptors that bind DNA as a monomer such as SF-1, NGFI-B, ERR, ROR, TLL and Rev-Erb. By choosing to shuffle only receptors of this type, the gene regulation system of this invention first allows the novel EcR LBD-based receptor to function without RXR. In this fashion, the EcR LBD-based receptor does not utilize endogenous RXR thus taking it away from endogenous receptors. Second, the amount of coding sequence that needs to be delivered to a host genome is essentially cut in half by preventing the need for RXR delivery. Given the size restrictions the currently known gene delivery vehicles have, any reduction in the amount of DNA to be delivered to a host in a gene therapy application would be very beneficial. For human gene therapy applications, a novel DBD is fused to a novel EcR-based LBD. To complete the receptor, an activation domain from a human transcription factor is added.

Unlike DNA shuffling, ITCHY does not rely on sequence homology for generation of chimeric genes. ITCHY generates a library of N- and C-terminal truncations of two genes by incremental digesting of their ends by exonuclease III (ExoIII). ExoIII catalyzes mononucleotide deletions from blunt or 5' overhangs. Therefore, a 3' overhang will protect an end of a sequence from digestion. This property of ExoIII can be exploited to obtain directional deletions of the genes of interest. For example, if ITCHY were to be performed on the estrogen receptor ("ER") and the progesterone receptor ("PR") genes, the desired library of mutants would not have an ER A/B domain ligated to a PR A/B domain. The desired product would either have the 5' region (amino-terminus) of the ER cDNA ligated to the 3' region (carboxy-terminus) of the PR cDNA or the 5' region of the PR cDNA ligated to the 3' region of the ER cDNA. Directionally deleting the parental sequences prevents unwanted ligations from occurring. During the ExoIII reaction, small aliquots are removed at short intervals and the enzyme inactivated so that at the termination of the entire procedure, a complete library of 1 base pair deletions along the length of the cDNAs is obtained. This library of fragments is then ligated together creating a new library of chimeric genes. The products of ITCHY can display a large range of size variation. For purposes of this invention, the recombinations that take place in the DEF domains of the EcR sequences and the C domain of the monomeric human nuclear receptors mentioned above are important for human gene therapy applications. Human DNA binding domains which may be useful in this process include, for example, mitochondrial transcription factor A ("mt-TFA"). It may also be useful to tether two DBDs which do not normally heterodimerize with short amino acid sequences to produce unique DBDs.

In comparison to DNA shuffling above, despite the fact that ITCHY generates only one crossover or recombination between two genes, it results in the generation of all possible crossovers because the technique is not based on sequence homology. This results in a more diverse sequence space to screen for improved function as compared to DNA shuffling. Given that there will be distinct regions within the C and E domains that share sequence homology, DNA shuffling will only be able to generate a limited number of shuffled regions. ITCHY, however, is not based on sequence homology and can result in all recombination possibilities. This is a very significant fact to consider for novel LBD and DBD engineering. In addition, the possibility exists to first perform ITCHY on several different gene pairs and then use that library, or a subset of that library, in DNA shuffling. In this manner, all possible recombinations would be obtained and the chances increased for identifying novel ligand and DNA binding domains.

After developing libraries of potential ligands, LBDs, and receptor DBDs, they must be evaluated for functional interactions. Once the receptor and ligand components for the multiple gene regulation system are assembled, it is necessary to test and validate the system in appropriate cell lines and assays.

The following process is utilized for such an evaluation. First, unique restriction sites are introduced into the starting DNA sequences on either end of the LBDs and on either end of the DBDs before mutagenesis/shuffling/ITCHY. The LBDs and the DBDs are then excised from the library of DNAs resulting from mutagenesis/shuffling/ITCHY. The resulting LBD and DBD libraries are then cloned into appropriate vectors and evaluated by identification of functional combinations of the ligands, LBDs, DBDs, and REs using one or more of the following processes:

a. LBD screening using an LBD translationally coupled to an antibiotic resistance gene by fusing an antibiotic resistance gene such as kanamycin to the mutated/shuffled/ITCHY LBDs. The DNA encoding the LBDs of the receptors in the libraries is excised using the unique restriction sites engineered between the C and D domains and at the 3' end of the library transcripts. These LBDs will be inserted into an expression cassette contained within a plasmid and a library of plasmids will be screened for full length translated proteins by transforming the library into *E. coli* and selecting for resistance to kanamycin. Plasmid DNA will be isolated from all the resistant colonies and used for mammalian cell screening.

b. LBD screening using a mammalian cell LBD and a one-hybrid system both for a complementary ligand and for the ability of the ligand bound receptor to activate transcription either as a homodimer or as a monomer. This process utilizes a cell line stably transfected with a reporter construct consisting of a multimerized GalL4 RE and a minimal promoter controlling expression of GFP. From the plasmid library isolated from kanamycin resistant colonies in step a. above, the region including the VP16 activation domain, Gal4 DBD and novel LBD is subcloned into a retroviral expression vector. This retrovirus also encodes a selectable antibiotic resistance gene. A library of retroviruses containing the DNA coding for these fusion proteins is prepared and used to infect the cell line described above that contains a GFP reporter under the control of a concatameric Gal4 RE. Cells with stably integrated retroviral DNA will be selected by antibiotic resistance. Additionally, these cells may be sorted by FACS for the expression of GFP. Cells expressing GFP in the absence of any exogenous ligand are discarded. The remaining population of cells is expanded and divided into groups in multi-well plates. In a high throughput assay, each group of cells is incubated with a different ligand from the ligand library. Those ligands activating GFP to the highest level are selected and used to screen the library of LBDs a second time. As before, the library of mutant receptors is divided into groups and each group incubated with a different ligand. However, as there are now be a limited number of ligands, each group of cells are sorted by FACS. The cells with the highest levels of GFP expression in response to ligand are collected, plated at low density and individual clones selected. The DNA encoding the LBD in each of these clones is isolated by PCR amplification and sequenced. These transcripts encode a LBD capable of mediating transcriptional activation in response to exposure to the ligand with which it was screened. These ligands are then be modified to optimize affinity and specificity for its complementary LBD. The modified ligands are evaluated as was the starting ligand library described above. If GFP is replaced with an antibiotic resistance gene in the reporter plasmid, the mammalian cell screening can also be done based on antibiotic selection. In this case, the retrovirally infected cells are grown in the presence of antibiotic and the surviving cells are isolated. As described above, the DNA encoding the LBD in each of the cell clones would be isolated and sequenced.
c. DBD screening using a DBD translationally coupled to an antibiotic resistance gene with strategy similar to the one described above for LBD screening to select against incompletely translated proteins. The DNA encoding the DBDs of the receptors in the libraries is excised using the unique restriction sites engineered between the A/B and C domains and the C and D domains. These DBDs are then inserted into the multiple cloning site of the various expression cassettes contained within plasmids.
d. DBD screening for cognate REs using a yeast one-hybrid assay in which the library of DBDs selected above is screened with a library of REs. The yeast strain used in this assay should not be sensitive to ganciclovir in the absence of thymidine kinase and also have the following nutritional requirements: leucine (leu), histidine (his), and uracil (ura) (i.e. the strain is deficient for LEU, HIS, and URA). The library of REs is a partially degenerate pool of oligonucleotides based on the consensus RE of the monomeric nuclear receptors used in the mutagenesis/shuffling/ITCHY procedures. This library is synthesized with restriction sites on each end of the oligonucleotides. Restriction digested oligonucleotides are cloned into a yeast expression vector at the 3' end of a reporter consisting of a LEU2/thymidine kinase fusion protein. This fusion protein allows for both the positive and negative selection of transcriptional activation. The reporter vector also contains a constitutively expressed URA selectable marker for positive selection of stable transformants on ura– medium. Expression of thymidine kinase is used to negatively select for activation of the RE by endogenous yeast factors by addition of the nucleoside analog ganciclovir to the growth medium. Following transformation, cells are grown on ura– ganciclovir+ medium. Cells containing REs capable of binding activated yeast transcription factors do not survive. The surviving transformed cells are the pooled. The VP16-nuclear receptor DBD cassette from the bacterial expression plasmids isolated above are excised and cloned under control of a constitutive promoter in a yeast expression vector. This vector contains a HIS selectable marker for transformation. Yeast transformed and selected for the presence of the RE-LEU2/thymidine kinase reporter is then be transformed a second time with this library of VP16-nuclear receptor DBD fusion proteins. The yeast is grown on ura– his– leu– medium to select for the presence of the reporter plasmid, for the plasmid containing the DBD library and for binding of the VP16-DBD protein to the RE in the reporter, respectively. The cells expressing a VP16-DBD protein that binds to the RE of the reporter will also express active thymidine kinase. However, ganciclovir is not added to the medium here, so these cells are not selected against. Instead, the cells are under positive growth selection due to expression of the LEU2 marker.
e. Screening of tethered transcription factor DBDs using a DNA RE to which the protein binds. The tethered transcription factors are expressed in *E. coli* as fusion proteins with an epitope tag. The epitope tag is used to construct an affinity column of the tethered DBDs. This column is used to select for a DNA RE. The candidate REs to be screened are contained within a synthesized oligonucleotide library. The oligonucleotides in this library contain the REs for each of the DBDs that comprise the tethered protein with a variable length random sequence spacer between the REs. Both ends of this library of oligonucleotides are a defined sequence. A different degenerate library is synthesized for each chimeric protein. A PCR based screening methodology is used to isolate the DNA sequences with highest binding affinity for the tethered DBDs. The tethered protein DBD affinity column is incubated with the library of REs, unbound oligonucleotides are washed away and bound oligonucleotides are eluted. The eluted oligonucleotides are candidate REs and are amplified by PCR using primers that anneal to the defined ends of the oligonucleotides. The resulting PCR products are applied to the affinity column. This procedure of oligonucleotide selection and PCR is repeated several, preferably 10 to 12, times. After the repeated screenings, the final mixture of oligonucleotides is cloned into a vector and the resulting pool of vectors transformed into *E. coli*. The oligonucleotide sequence in individual clones are determined by DNA sequencing. The sequences from multiple clones are aligned to determine a consensus binding site for each of the tethered DBDs. An oligonucleotide based on this consensus binding site is synthesized and used with the corresponding tethered DBD in the yeast assay described above. In this manner, the relative affinities between the RE/DBD combinations isolated using the mutagenized/shuffled/ITCHY products and the tethered DBDs is determined.

Each pair of the LBD variants identified in the screens described above is paired with a unique DBD identified above. The DNA encoding each of these new chimeric LBD/DBD variants is placed under the control of a constitutive promoter in a mammalian expression vector. The DNA response element for each of the DBDs of the chimeric LBD/DBD proteins is inserted upstream of a reporter gene in this same plasmid. Each plasmid includes an antibiotic resistance marker under the control of a constitutive promoter. The chimeric receptor variants and REs in each of these individual stable cell lines is characterized with respect to the level of reporter expression in the absence of ligand, as well as the fold induction of reporter activity in the presence of ligand.

The group of plasmids encoding functional chimeric receptors and their corresponding REs are then sequentially stably transfected into mammalian cells. After transfection of each plasmid, the cells are assayed for their response to the ligand(s) for the chimeric receptor(s) that the cells contain. Selection of cells with stable integration of these plasmids requires the use of genes encoding proteins rendering cells resistant to multiple antibiotics (hygromycin, neomycin, puromycin, bleomycin, blasticidin). Assay for inducible gene expression requires multiple reporter proteins such as, for example, firefly luciferase, Renilla luciferase, β-galactosidase, alkaline phosphatase, chloramphenicol acetyltransferase, and growth hormones. These materials are all readily available.

After the DNA encoding all of the receptors and their corresponding response elements are stably integrated within the genome, the resulting cell line is used to assess the cross reactivity (orthogonality) between different ligands and different chimeric receptors in the context of the same cell. The cells are incubated with individual ligands and the activity of all the reporter proteins assayed. Cells are also be incubated with different combinations of the ligands with subsequent assay of all the reporter proteins.

Preferably, the ligand/LBD interaction for each of the ligand/LBD pairs have Kds between 0.1 and 1000 nm. More preferably, the ligand/LBD interaction for each of the ligand/LBD pairs have Kds between 0.1 and 100 nm. Even more preferably, the ligand/LBD interaction for each of the ligand/LBD pairs have Kds between 0.1 and 10 nm. Most preferably, the ligand/LBD interaction for each of the ligand/LBD pairs have Kds between 0.1 and 1.0 nm.

The multiple gene regulation systems of this invention are useful not only in the area of gene modulation itself, but also in other major areas such as, for example, proteomics, functional genomics, gene therapies, cell-based high throughput assays, biosensors, toxicology screening, and large-scale protein production.

Specifically, functional genomics and proteomics are hampered today by their inability to deal with multifactorial phenotypes in which multiple genes are involved. There are numerous examples. Some of the most dramatic include, for example, signal transduction cascades, such as the wnt/catenin pathway, where more than 20 proteins are involved. This pathway has been implicated in cancer, neurodegenerative diseases, immune system dysfunctions and others. Dissecting the interactions among members of the pathway in functional genomic and proteomic studies would be greatly facilitated by the advent of a multiple gene control system. The researcher could then regulate multiple factors simultaneously and determine key interactions more precisely than with the current state of the art approaches that are based on gene knock-out, knock-in or mutagenesis strategies.

Similarly, certain gene therapies will require more than one gene to be regulated. For example, generating immune responses to a cancer through the introduction of cytokine and antigen gene cocktails would require a multiple regulation system. This enables the therapy to function safely and in a quantitative, integrated manner.

The multiple gene regulation systems of this invention have many advantages over other gene induction systems currently in use, depending on the application. In proteomics and functional genomics, it changes significantly the way in which cell phenotypes and gene function are analyzed. Instead of one gene/protein at a time, it enables the analysis of entire molecular pathways in cells, which is much closer to what actually happens in a real organism. In protein production or high throughput screening, the technology is a new infrastructure for parallel protein production or for screening against multiple targets simultaneously.

Host cells and Non-Human Organisms

Another aspect of the present invention relates to an isolated host cell comprising a multiple gene regulation system according to the invention. As described above, the a multiple gene regulation systems of the present invention may be used to modulate gene expression in a host cell. Expression in transgenic host cells may be useful for the expression of various genes of interest. Applicants' invention provides for modulation of gene expression in prokaryotic and eukaryotic host cells. Expression in transgenic host cells is useful for the expression of various polypeptides of interest including but not limited to antigens produced in plants as vaccines, enzymes like alpha-amylase, phytase, glucanase, and xylanase, genes for resistance against insects, nematodes, fungi, bacteria, viruses, and abiotic stresses, antigens, nutraceuticals, pharmaceuticals, vitamins, genes for modifying amino acid content, herbicide resistance, cold, drought, and heat tolerance, industrial products, oils, protein, carbohydrates, antioxidants, male sterile plants, flowers, fuels, other output traits, therapeutic polypeptides, pathway intermediates; for the modulation of pathways already existing in the host for the synthesis of new products heretofore not possible using the host; cell based assays; functional genomics assays, biotherapeutic protein production, proteomics assays, and the like. Additionally the gene products may be useful for conferring higher growth yields of the host or for enabling an alternative growth mode to be utilized.

In a specific embodiment, the isolated host cell is a prokaryotic host cell or a eukaryotic host cell. In another specific embodiment, the isolated host cell is an invertebrate host cell or a vertebrate host cell. Preferably, the isolated host cell is selected from the group consisting of a bacterial cell, a fungal cell, a yeast cell, a nematode cell, an insect cell, a fish cell, a plant cell, an avian cell, an animal cell, and a mammalian cell. More preferably, the isolated host cell is a yeast cell, a nematode cell, an insect cell, a plant cell, a zebrafish cell, a chicken cell, a hamster cell, a mouse cell, a rat cell, a rabbit cell, a cat cell, a dog cell, a bovine cell, a goat cell, a cow cell, a pig cell, a horse cell, a sheep cell, a simian cell, a monkey cell, a chimpanzee cell, or a human cell.

Examples of preferred host cells include, but are not limited to, fungal or yeast species such as *Aspergillus, Trichoderma, Saccharomyces, Pichia, Candida, Hansenula*, or bacterial species such as those in the genera *Synechocystis, Synechococcus, Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium* and *Klebsiella*; plant species selected from the group consisting of an apple, *Arabidopsis*, bajra, banana, barley, beans, beet, blackgram, chickpea, chili, cucumber, eggplant, favabean, maize, melon, millet, mungbean, oat, okra, *Panicum*, papaya, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat; animal; and mammalian host cells.

In a specific embodiment, the isolated host cell is a yeast cell selected from the group consisting of a *Saccharomyces*, a *Pichia*, and a *Candida* host cell.

In another specific embodiment, the isolated host cell is a *Caenorhabdus elegans* nematode cell.

In another specific embodiment, the isolated host cell is a plant cell selected from the group consisting of an apple, *Arabidopsis*, bajra, banana, barley, beans, beet, blackgram, chickpea, chili, cucumber, eggplant, favabean, maize, melon, millet, mungbean, oat, okra, *Panicum*, papaya, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat cell.

In another specific embodiment, the isolated host cell is a zebrafish cell.

In another specific embodiment, the isolated host cell is a chicken cell.

In another specific embodiment, the isolated host cell is a mammalian cell selected from the group consisting of a hamster cell, a mouse cell, a rat cell, a rabbit cell, a cat cell, a dog cell, a bovine cell, a goat cell, a cow cell, a pig cell, a horse cell, a sheep cell, a monkey cell, a chimpanzee cell, and a human cell.

Host cell transformation is well known in the art and may be achieved by a variety of methods including but not limited to electroporation, viral infection, plasmid/vector transfection, non-viral vector mediated transfection, *Agrobacterium*-mediated transformation, particle bombardment, and the like. Expression of desired gene products involves culturing the transformed host cells under suitable conditions and inducing expression of the transformed gene. Culture conditions and gene expression protocols in prokaryotic and eukaryotic cells are well known in the art (see General Methods section of Examples). Cells may be harvested and the gene products isolated according to protocols specific for the gene product.

In addition, a host cell may be chosen that modulates the expression of the transfected polynucleotides, or modifies and processes the polypeptide products in a specific fashion desired. Different host cells have characteristic and specific mechanisms for the translational and post-translational processing and modification [e.g, glycosylation, cleavage (e.g., of signal sequence)] of proteins. Appropriate cell lines or host systems can be chosen to ensure the desired modification and processing of the foreign protein expressed. For example, expression in a bacterial system can be used to produce a non-glycosylated core protein product. However, a polypeptide expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, the polypeptide's activity. Furthermore, different vector/host expression systems may affect processing reactions, such as proteolytic cleavages, to a different extent.

Applicants' invention also relates to a non-human organism comprising an isolated host cell according to the invention. In a specific embodiment, the non-human organism is a prokaryotic organism or a eukaryotic organism. In another specific embodiment, the non-human organism is an invertebrate organism or a vertebrate organism.

Preferably, the non-human organism is selected from the group consisting of a bacterium, a fungus, a yeast, a nematode, an insect, a fish, a plant, a bird, an animal, and a mammal. More preferably, the non-human organism is a yeast, a nematode, an insect, a plant, a zebrafish, a chicken, a hamster, a mouse, a rat, a rabbit, a cat, a dog, a bovine, a goat, a cow, a pig, a horse, a sheep, a simian, a monkey, or a chimpanzee.

In a specific embodiment, the non-human organism is a yeast selected from the group consisting of *Saccharomyces*, *Pichia*, and *Candida*.

In another specific embodiment, the non-human organism is a *Caenorhabdus elegans* nematode.

In another specific embodiment, the non-human organism is a plant selected from the group consisting of an apple, *Arabidopsis*, bajra, banana, barley, beans, beet, blackgram, chickpea, chili, cucumber, eggplant, favabean, maize, melon, millet, mungbean, oat, okra, *Panicum*, papaya, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat.

In another specific embodiment, the non-human organism is a *Mus musculus* mouse.

Measuring Gene Expression/Transcription

One useful measurement of the multiple gene regulation systems and methods of the present invention is that of the transcriptional state of the cell including the identities and abundances of RNA, preferably mRNA species. Such measurements are conveniently conducted by measuring cDNA abundances by any of several existing gene expression technologies.

Nucleic acid array technology is a useful technique for determining differential mRNA expression. Such technology includes, for example, oligonucleotide chips and DNA microarrays. These techniques rely on DNA fragments or oligonucleotides which correspond to different genes or cDNAs which are immobilized on a solid support and hybridized to probes prepared from total mRNA pools extracted from cells, tissues, or whole organisms and converted to cDNA. Oligonucleotide chips are arrays of oligonucleotides synthesized on a substrate using photolithographic techniques. Chips have been produced which can analyze for up to 1700 genes. DNA microarrays are arrays of DNA samples, typically PCR products, that are robotically printed onto a microscope slide. Each gene is analyzed by a full or partial-length target DNA sequence. Microarrays with up to 10,000 genes are now routinely prepared commercially. The primary difference between these two techniques is that oligonucleotide chips typically utilize 25-mer oligonucleotides which allow fractionation of short DNA molecules whereas the larger DNA targets of microarrays, approximately 1000 base pairs, may provide more sensitivity in fractionating complex DNA mixtures.

Another useful measurement of Applicants' multiple gene regulation systems and methods of the invention is that of determining the translation state of the cell by measuring the abundances of the constituent protein species present in the cell using processes well known in the art.

Where identification of genes associated with various physiological functions is desired, an assay may be employed in which changes in such functions as cell growth, apoptosis, senescence, differentiation, adhesion, binding to a specific molecules, binding to another cell, cellular organization, organogenesis, intracellular transport, transport facilitation, energy conversion, metabolism, myogenesis, neurogenesis, and/or hematopoiesis is measured.

In addition, selectable marker or reporter gene expression may be used to measure gene expression using Applicants' invention.

Other methods to detect the products of gene expression are well known in the art and include Southern blots (DNA detection), dot or slot blots (DNA, RNA), northern blots (RNA), RT-PCR (RNA), western blots (polypeptide detection), and ELISA (polypeptide) analyses. Although less preferred, labeled proteins can be used to detect a particular nucleic acid sequence to which it hybridizes.

In some cases it is necessary to amplify the amount of a nucleic acid sequence. This may be carried out using one or more of a number of suitable methods including, for example, polymerase chain reaction ("PCR"), ligase chain reaction ("LCR"), strand displacement amplification ("SDA"), transcription-based amplification, and the like. PCR is carried out in accordance with known techniques in which, for example, a nucleic acid sample is treated in the presence of a heat stable DNA polymerase, under hybridizing conditions, with one pair of oligonucleotide primers, with one primer hybridizing to one strand (template) of the specific sequence to be detected. The primers are sufficiently complementary to each template strand of the specific sequence to hybridize therewith. An extension product of each primer is synthesized and is complementary to the nucleic acid template strand to which it hybridized. The extension product synthesized from each primer can also serve as a template for further synthesis of extension products using the same primers. Following a sufficient number of rounds of synthesis of extension products, the sample may be analyzed as described above to assess whether the sequence or sequences to be detected are present.

The present invention may be better understood by reference to the following non-limiting Examples, which are provided as exemplary of the invention.

EXAMPLES

General Methods

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989")]; *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Conventional cloning vehicles include pBR322 and pUC type plasmids and phages of the M13 series. These may be obtained commercially (Bethesda Research Laboratories).

For ligation, DNA fragments may be separated according to their size by agarose or acrylamide gel electrophoresis, extracted with phenol or with a phenol/chloroform mixture, precipitated with ethanol and then incubated in the presence of phage T4 DNA ligase (Biolabs) according to the supplier's recommendations.

The filling in of 5' protruding ends may be performed with the Klenow fragment of *E. coli* DNA polymerase I (Biolabs) according to the supplier's specifications. The destruction of 3' protruding ends is performed in the presence of phage T4 DNA polymerase (Biolabs) used according to the manufacturer's recommendations. The destruction of 5' protruding ends is performed by a controlled treatment with S1 nuclease.

Mutagenesis directed in vitro by synthetic oligodeoxynucleotides may be performed according to the method developed by Taylor et al. [Nucleic Acids Res. 13 (1985) 8749-8764] using the kit distributed by Amersham.

The enzymatic amplification of DNA fragments by PCR [Polymerase-catalyzed Chain Reaction, Saiki R. K. et al., Science 230 (1985) 1350-1354; Mullis K. B. and Faloona F. A., Meth. Enzym. 155 (1987) 335-350] technique may be performed using a "DNA thermal cycler" (Perkin Elmer Cetus) according to the manufacturer's specifications.

Verification of nucleotide sequences may be performed by the method developed by Sanger et al. [Proc. Natl. Acad. Sci. USA, 74 (1977) 5463-5467] using the kit distributed by Amersham.

Plasmid DNAs may be purified by the Qiagen Plasmid Purification System according to the manufacture's instruction.

Manipulations of genetic sequences may be accomplished using the suite of programs available from the Genetics Computer Group Inc. (Wisconsin Package Version 9.0, Genetics Computer Group (GCG), Madison, Wis.). Where the GCG program "Pileup" is used the gap creation default value of 12, and the gap extension default value of 4 may be used. Where the CGC "Gap" or "Bestfit" programs is used the default gap creation penalty of 50 and the default gap extension penalty of 3 may be used. In any case where GCG program parameters are not prompted for, in these or any other GCG program, default values may be used.

The meaning of abbreviations is as follows: "h" means hour(s), "min" means minute(s), "sec" means second(s), "d" means day(s), "µl" means microliter(s), "ml" means milliliter(s), "L" means liter(s), "µM" means micromolar, "mM" means millimolar, "µg" means microgram(s), "mg" means milligram(s), "A" means adenine or adenosine, "T" means thymine or thymidine, "G" means guanine or guanosine, "C" means cytidine or cytosine, "xg" means times gravity, "nt" means nucleotide(s), "aa" means amino acid(s), "bp" means base pair(s), "kb" means kilobase(s), "k" means kilo, "µ" means micro, and "° C." means degrees Celsius.

Example 1

This Example describes the construction of several gene expression cassettes for use in a multiple inducible gene expression system according to the invention. Applicants constructed several gene expression cassettes based on the spruce budworm *Choristoneura fumiferana* EcR ("CfEcR"), fruit fly *Drosophila melanogaster* EcR ("DmEcR"), green leafhopper *Nephotetix cincticeps* ecdysone receptor ("NcEcR"), mouse *Mus musculus* retinoid X receptor isoform a ("MmRXRα"), and locust *Locusta migratoria* invertebrate RXR homolog ultraspiracle protein ("LmUSP"). The prepared receptor constructs comprise a ligand binding domain of either an EcR or a vertebrate RXR; and a GAL4 DNA binding domain (DBD) or a VP16 transactivation domain (AD). The reporter constructs include a reporter gene, luciferase (Luc) or secreted alkaline phosphatase (SEAP), operably linked to a synthetic promoter construct that comprises a GAL4 response element to which the GAL4 DBD binds. Various combinations of these receptor and reporter constructs were cotransfected into mammalian cells as described infra.

Gene Expression Cassettes: Gene expression cassettes for use in two dual switch ecdysone receptor-based inducible gene expression systems were constructed as followed, using standard cloning methods available in the art. The following is a brief description of preparation and composition of each switch used in the Examples described herein.

1.1—GAL4DmEcR-CDEF/VP16MmRXR-LmUSP-EFchimera and LexACfEcR-CDEF/VP16MmRXR-LmUSP-EFchimera: A polynucleotide encoding the C, D, E, and F domains from fruit fly *Drosophila melanogaster* EcR ("DmEcR-CDEF"; SEQ ID NO: 1) was fused to a polynucleotide encoding a GAL4 DNA binding domain ("Gal4DNABD" or "Gal4DBD"; SEQ ID NO: 2) and placed under the control of a cytomegalovirus (CMV) promoter/enhancer (SEQ ID NO: 3). A polynucleotide encoding the C, D, E, and F domains from spruce budworm *Choristoneura fumiferana* EcR ("CfEcR-CDEF"; SEQ ID NO: 4) was fused to a polynucleotide encoding a LexA DNA binding domain ("LexADNABD" or "LexADBD"; SEQ ID NO: 5) and placed under the control of a cytomegalovirus (CMV) promoter/enhancer (SEQ ID NO: 3). A polynucleotide encoding a chimeric EF domains polypeptide from mouse *Mus musculus* retinoid X receptor isoform α ("MmRXRα") and locust *Locusta migratoria* ultraspiracle protein ("LmUSP-EF") (SEQ ID NO: 6) was fused to a polynucleotide encoding a transactivation domain from VP16 ("VP16AD"; SEQ ID NO: 7) and placed under the control of a CMV promoter/enhancer (SEQ ID NO: 3). Six consensus GAL4 response element binding sites ("6×GAL4RE"; SEQ ID NO: 8) were fused to an albumin minimal promoter (SEQ ID NO: 9) and placed upstream of the secreted alkaline phosphatase (SEAP) gene (SEQ ID NO: 10). Eight consensus LexA response element binding sites ("8opLexARE"; SEQ ID NO: 11) were fused to a synthetic TATAA (SEQ ID NO: 12) and placed upstream of the luciferase gene (SEQ ID NO: 13).

1.2—GAL4CfEcR-DEF/VP16MmRXRα-EF and GAL4NcEcR-CDE/VP16MmRXRα-EF: This construct was prepared as follows. A polynucleotide encoding the D, E, and F domains from spruce budworm *Choristoneura fumiferana* EcR ("CfEcR-DEF"; SEQ ID NO: 14) was fused to a polynucleotide encoding a GAL4DNA binding domain ("GAL4DBD"; SEQ ID NO: 2) and placed under the control of a cytomegalovirus (CMV) promoter/enhancer (SEQ ID NO: 3). A polynucleotide encoding the C, D and E domains from green leafhopper *Nephotetix cincticeps* ecdysone receptor ("NcEcR-CDE"; SEQ ID NO: 15) was fused to a polynucleotide encoding a GAL4DNA binding domain ("GAL4DBD"; SEQ ID NO: 2) and placed under the control of a cytomegalovirus (CMV) promoter/enhancer (SEQ ID NO: 3). A polynucleotide encoding the E and F domains from mouse *Mus musculus* retinoid X receptor isoform α ("MmRXRα"; SEQ ID NO: 16) was fused to a polynucleotide encoding a transactivation domain from VP16 ("VP16AD"; SEQ ID NO: 7) and placed under the control of a CMV promoter/enhancer (SEQ ID NO: 3). Six consensus GAL4 response element binding sites ("6×GAL4RE"; SEQ ID NO: 8) were fused to a synthetic TATAA (SEQ ID NO: 12) and placed upstream of the firefly luciferase gene (SEQ ID NO: 13).

The resulting dual switch systems of Examples 1.1 and 1.2 were tested for activity by transfecting them into NIH3T3 cells or CHO cells in the presence of ponasterone A (PonA) steroidal ligand and N-(2-ethyl-3-methoxybenzoyl)-N'-(3,5-dimethylbenzoyl)-N'-tert-butylhydrazine (GS™-E) non-steroidal ligand.

Ligands: The steroidal ligand ponasterone A was purchased from Sigma Chemical Company. The non-steroidal ligand N-(2-ethyl-3-methoxybenzoyl)-N'-(3,5-dimethylbenzoyl)-N'-tert-butylhydrazine (GS™-E non-steroidal ligand) is a synthetic stable ecdysteroid ligand synthesized at Rohm and Haas Company. Both ligands were dissolved in DMSO and the final concentration of DMSO was maintained at 0.1% in both controls and treatments.

Transfections: DNAs corresponding to the dual switch constructs outlined in Examples 1.1 and 1.2 were transfected into mouse NIH3T3 cells (ATCC; Example 1.1) or CHO cells (ATCC; Example 1.2) as follows. Standard methods for culture and maintenance of the cells were followed. Cells were harvested when they reached 50% confluency and plated in 6-, 12- or 24-well plates at 125,000, 50,000, or 25,000 cells, respectively, in 2.5, 1.0, or 0.5 ml of growth medium containing 10% fetal bovine serum (FBS), respectively. The next day, the cells were rinsed with growth medium and transfected for four hours. Superfect™ (Qiagen Inc.) was used for 3T3 cells and LipofectAMINE™ (LifeTechnologies) was used for CHO cells as the transfection reagents. For 12-well plates, 4 µl of Superfect™ or LipofectAMINE™ was mixed with 100 µl of growth medium. One µg of reporter construct and 0.25 µg of each receptor construct of the receptor pair to be analyzed were added to the transfection mix. A second reporter construct was added [pTKRL (Promega), 0.1 µg/transfection mix] that comprises a Renilla luciferase gene operably linked and placed under the control of a thymidine kinase (TK) constitutive promoter and was used for normalization. The contents of the transfection mix were mixed in a vortex mixer and let stand at room temperature for 30 minutes. At the end of incubation, the transfection mix was added to the cells maintained in 400 µl growth medium. The cells were maintained at 37° C. and 5% $CO_2$ for four hours. At the end of incubation, 500 µl of growth medium containing 20% FBS and either dimethylsulfoxide (DMSO; control) or a DMSO solution of steroidal or non-steroidal ligand was added and the cells were maintained at 37° C. and 5% $CO_2$ for 48 hours. The cells were harvested and reporter activity was assayed. The same procedure was followed for 6 and 24 well plates as well except all the reagents were doubled for 6 well plates and reduced to half for 24-well plates.

Reporter Assays: Cells were harvested 48 hours after adding ligands and reporter activities were quantified using the Dual-luciferase™ reporter assay system from Promega Corporation. 125 µl of passive lysis buffer (part of Dual-luciferase™ reporter assay system from Promega Corporation) were added to each well of the 24-well plate. The plates were placed on a rotary shaker for 15 minutes. Twenty µl of lysate were assayed. Luciferase activity was measured using Dual-luciferase™ reporter assay system from Promega Corporation following the manufacturer's instructions. Alkaline phosphatase activity was measured using the Phospholight™ assay kit from TROPIX following the manufacturer's instructions. All luciferase and alkaline phosphatase activities were normalized using Renilla luciferase as a standard. Fold activities were calculated by dividing normalized relative light units ("RLU") in ligand treated cells with normalized RLU in DMSO treated cells (untreated control).

Example 2

This Example describes the ability of a dual switch gene expression system of Applicants' invention to modulate expression of two reporter gene expression cassettes, wherein the two reporter gene expression cassettes are regulated independently by two different ligands. Specifically, one reporter gene expression cassette is inducibly regulated by a steroid ligand and the other reporter gene expression cassette is inducibly regulated by a non-steroid ligand. Briefly, Applicants prepared a dual switch inducible gene expression system as described above in Example 1.1. The resulting dual switch system was then tested in NIH3T3 mammalian cells as follows.

DNAs corresponding to the dual switch constructs outlined in Example 1.1 were transfected into mouse NIH3T3 cells (ATCC) as described in Example 1. At the end of the transfection incubation period, 250 µl of growth medium containing 20% FBS and either dimethylsulfoxide (DMSO; control) or a DMSO solution of 0.02, 0.1, 0.5, or 2.5 µM PonA steroidal ligand and/or GS™-E [N-(2-ethyl-3-methoxybenzoyl) N'-(3,5-dimethylbenzoyl)-N'-tert-butylhydrazine] non-steroidal ligand was added and the cells were maintained at 37° C., and 5% $CO_2$ for 48 hours. The cells were harvested and reporter activities were assayed as described above.

Figure 1B:
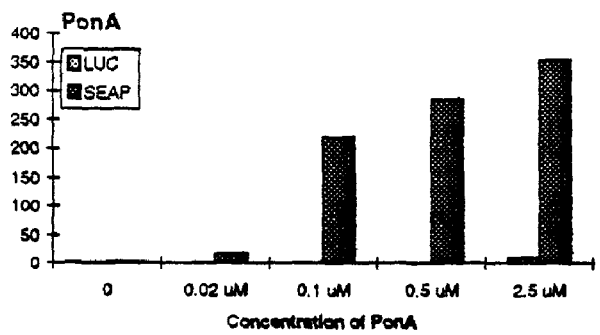
Figure 1C:
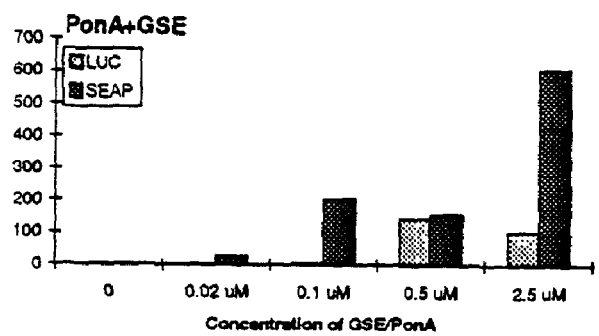

As shown in FIG. 1, when the cells were treated with non-steroidal ligand alone, only luciferase activity was induced (see FIG. 1A). When the cells were treated with steroidal ligand alone, only SEAP reporter activity was induced (see FIG. 1B). When the cells were treated with both steroidal and non-steroidal ligands, both reporter gene activities were induced (see FIG. 1C). This Example demonstrates a multiple inducible gene expression system comprising at two individually operable gene expression systems, one Dipteran EcR-based (DmEcR) and the other Lepidopteran EcR-based (CfEcR).

Example 3

This Example describes the ability of a dual switch gene expression system of Applicants' invention to modulate expression of two reporter gene expression cassettes, wherein the two reporter gene expression cassettes are regulated independently by two different ligands. In particular, one reporter gene expression cassette is inducibly regulated by a steroid ligand and the other reporter gene expression cassette is inducibly regulated by a non-steroid ligand. Briefly, Applicants prepared a dual switch inducible gene expression system as described above in Example 1.2. The resulting dual switch system was then tested in Chinese hamster ovary CHO cells as follows.

DNAs corresponding to the dual switch constructs outlined in Example 1.2 were transfected into hamster CHO cells (ATCC) as described in Example 1. CHO cells were transfected with 1) GAL4CfEcR-DEF/VP16MmRXRα-EF and pFRLuc, or 2) GAL4NcEcR-CDE/VP16MmXRYα-EF and pFRLuc. At the end of the transfection incubation period, 250 µl of growth medium containing 20% FBS and either dimethylsulfoxide (DMSO; control) or a DMSO solution of 0.1, 1, 5, or 10 μM PonA steroidal ligand or GS™-E [N-(2-ethyl-3-methoxybenzoyl)N'-(3,5-dimethylbenzoyl)-N'-tert-butylhydrazine] non-steroidal ligand was added and the cells were maintained at 37° C. and 5% $CO_2$ for 48 hours. The cells were harvested and reporter activity was assayed as described above.

Figure 2:
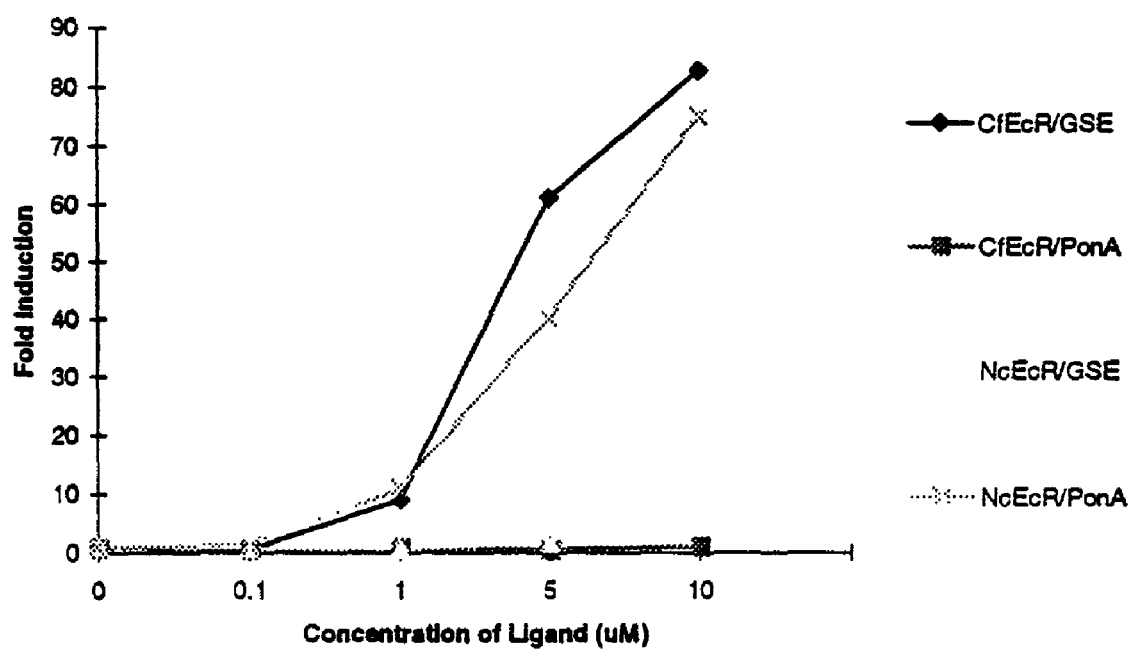
FIG. 2: Transactivation of reporter genes through GAL4CfEcR-DEF or GAL4NcEcR-CDE transfected into CHO cells along with VP16MmRXRα-EF and pFRLuc reporter by PonA or GS™-E.

As shown in FIG. 2, when the cells transfected with GAL4CfEcR-DEF/VP16MmRXRα-EF and pFRLuc were treated with non-steroidal ligand alone, luciferase activity regulated by CfEcR-DEF was induced (see CfEcR/GSE of FIG. 2), however treatment of these transfected cells with the steroid ligand PonA did not induce reporter gene expression (see CfEcR/PonA of FIG. 2). When the cells transfected with GAL4NcEcR-CDE/VP16MmRXRα-EF and pFRLuc were treated with steroidal ligand alone, luciferase reporter activity regulated by NcEcR-DE was induced (see NcEcR/PonA of FIG. 2), however treatment of these transfected cells with non-steroidal ligand does not induce reporter gene expression (see NcEcR/GSE of FIG. 2). The insensitivity of CfEcR-DEF to PonA and the insensitivity of NcEcR-CDE to GS™-E permits the two gene expression modulation systems described here to be orthogonally modulated. Thus, this Example demonstrates two individually operable gene expression systems, one Lepidopteran EcR-based (CfEcR) and the other Homopteran EcR-based (NcEcR), for use in a multiple inducible gene expression system of the invention.

We claim:

1. A multiple inducible gene regulation system consisting of two orthogonal gene regulation systems, wherein each of said orthogonal gene regulation systems comprises:
   i) a first polynucleotide encoding a first polypeptide comprising:
      A) a DNA binding domain, and
      B) an ecdysone receptor ligand binding domain; and
   ii) a second polynucleotide encoding a second polypeptide comprising:
      C) a nuclear receptor ligand binding domain capable of forming a dimer with the ecdysone receptor ligand binding domain of said first polypeptide, and
      D) a transactivation domain; and
   iii) a third polynucleotide encoding a third polypeptide, wherein said third polynucleotide is operatively linked to a response element,
   wherein binding of the DNA binding domain of said first polypeptide to said response element results in expression of said third polypeptide.

2. A virus comprising the multiple inducible gene regulation system of claim 1.

3. An isolated host cell comprising the multiple inducible gene regulation system of claim 1.

4. A multiple inducible gene regulation system consisting of two orthogonal gene regulation systems wherein each of said gene regulation systems comprises:
   i) a first polypeptide comprising:
      A) a DNA binding domain, and
      B) an ecdysone receptor ligand binding domain; and
   ii) a second polypeptide comprising:
      C) a nuclear receptor ligand binding domain capable of forming a dimer with the ecdysone receptor ligand binding domain of said first polypeptide, and
      D) a transactivation domain; and
   iii) a polynucleotide comprising
      an exogenous or endogenous gene and a response element wherein
      said exogenous or endogenous gene is under the control of said response element and, wherein
      binding of the DNA binding domain of said first polypeptide to said response element in the presence of a ligand results in expression of said exogenous or endogenous gene.

5. An isolated host cell comprising the multiple inducible gene regulation system of claim 4.

6. A vector comprising the multiple inducible gene regulation system of claim 1.

7. The isolated host cell of claim 3, wherein the host cell is a bacterial cell, a fungal cell, a yeast cell, a plant cell, an animal cell, a mammalian cell, a mouse cell, or a human cell.

8. The isolated host cell of claim 7, wherein the host cell is a human cell.

9. The isolated host cell of claim 5, wherein the host cell is a bacterial cell, a fungal cell, a yeast cell, a plant cell, an animal cell, a mammalian cell, a mouse cell, or a human cell.

10. The isolated host cell of claim 9, wherein the host cell is a human cell.

11. The multiple inducible gene modulation system of claim 1, wherein said nuclear receptor ligand binding domain is selected from the group consisting of a vertebrate retinoid X receptor ligand binding domain; an invertebrate retinoid X receptor ligand binding domain; an ultraspiracle protein ligand binding domain; and a chimeric ligand binding domain comprising two polypeptide fragments, wherein the first polypeptide fragment is from a vertebrate retinoid X receptor ligand binding domain, an invertebrate retinoid X receptor ligand binding domain, or an ultraspiracle protein ligand binding domain, and the second polypeptide fragment is from a different vertebrate retinoid X receptor ligand binding domain, invertebrate retinoid receptor ligand binding domain, or an ultraspiracle protein ligand binding domain.

12. The multiple inducible gene modulation system of claim 1, wherein said ecdysone receptor ligand binding domain is selected from the group consisting of a Lepidopteran ecdysone receptor ligand binding domain, a Dipteran ecdysone receptor ligand binding domain, an Arthropod ecdysone receptor ligand binding domain, an Orthopteran ecdysone receptor ligand binding domain, a Homopteran ecdysone receptor ligand binding domain, a Hemipteran ecdysone receptor ligand binding domain, a spruce budworm *Choristoneura fumiferana* ecdysone receptor ligand binding domain, a yellow meal worm *Tenebrio molitor* ecdysone receptor ligand binding domain, a tobacco hornworm *Manduca sexta* ecdysone receptor ligand binding domain, a tobacco budworm *Heliothies virescens* ecdysone receptor ligand binding domain, a golmidge *Chironomus tentans* ecdysone receptor ligand binding domain, a silkworm *Bombyx mori* ecdysone receptor ligand binding domain, a squinting bush brown *Bicyclus anynana* ecdysone receptor ligand binding domain, a buckeye *Junonia coenia* ecdysone receptor ligand binding domain, a fruit fly *Drosophila melanogaster* ecdysone receptor ligand binding domain, a yellow fever mosquito *Aedes aegypti* ecdysone receptor ligand binding domain, a blowfly *Lucilia capitata* ecdysone receptor ligand binding domain, a sheep blowfly *Lucilia cuprina* ecdysone receptor ligand binding domain, a blowfly *Calliphora vicinia* ecdysone receptor ligand binding domain, a Mediterranean fruit fly *Ceratins capitata* ecdysone receptor ligand binding domain, a locust *Locusta migratoria* ecdysone receptor ligand binding domain, an aphid *Myzus persicae* ecdysone receptor ligand binding domain, a fiddler crab *Celuca pugilator* ecdysone receptor ligand binding domain, an ixodid tick *Amblyomma americanum* ecdysone receptor ligand binding domain, and a white fly *Bamecia argentifoli* ecdysone receptor ligand binding domain.

13. The multiple inducible gene modulation system of claim 12, wherein said ecdysone receptor ligand binding domain is a spruce budworm *Choristoneura fumiferana* ecdysone receptor ligand binding domain.

14. The multiple inducible gene modulation system of claim 1, wherein said DNA binding domain is selected from the group consisting of a GAL4 DNA binding domain, a LexA DNA binding domain, a transcription factor DNA binding domain, a Group H nuclear receptor member DNA binding domain, a steroid/thyroid hormone nuclear receptor superfamily member DNA binding domain, a bacterial LacZ DNA binding domain, and an ecdysone receptor DNA binding domain.

15. The multiple inducible gene modulation system of claim 1, wherein said transactivation domain is selected from the group consisting of a Group H nuclear receptor member transactivation domain, a steroid/thyroid hormone nuclear receptor transactivation domain, a polyglutamine transactivation domain, a basic or acidic amino acid transactivation domain, a VP16 transactivation domain, a GAL4 transactivation domain, an NF-KB transactivation domain, a BP64 transactivation domain a B42 acidic transactivation domain, and a p65 transactivation domain.

16. The virus of claim 2, wherein said virus is an adenovirus, adeno-associated virus or retrovirus.

17. The vector of claim 6, wherein said vector is a plasmid.

18. The vector of claim 6, wherein said vector is an expression vector.

19. The vector of claim 6, wherein said vector is a viral vector.

20. The vector of claim 19, wherein said vector is an adenovirus vector, adeno-associated virus, or retrovirus.

21. The isolated host cell of claim 3, wherein said cell is a mammalian cell.

22. The isolated host cell of claim 21, wherein said mammalian cell is selected from the group consisting of a hamster cell, a murine cell, a monkey cell, a mouse cell, a rat cell, a rabbit cell, a cat cell, a dog cell, a bovine cell, a goat cell, a pig cell, a horse cell, a sheep cell, a monkey cell and a chimpanzee cell.

23. The isolated host cell of claim 3, wherein the host cell is selected from the group consisting of an *Aspergillus* cell, a *Trichoderma* cell, a *Saccharomyces* cell, a *Pichia* cell, a *Candida* cell, and a *Hansenula* cell.

24. The isolated host cell of claim 3, wherein the host cell is selected from the group consisting of a *Syneechocystis* cell, a *Synechococcus* cell, a *Salmonella* cell, a *Bacillus* cell, an *Acinetobacter* cell, a *Rhodococcus* cell, a *Streptomyces* cell, an *Escherichia* cell, a *Pseudomonas* cell, a *Methylomonas* cell, a *Methylobacter* cell, an *Alcaligenes* cell, a *Synechocystis* cell, an *Anabaena* cell, a *Thiobacillus* cell, a *Methanobacterium* cell and a *Klebsiella* cell.

25. The isolated host cell of claim 3, wherein the host cell is a plant cell.

26. The isolated host cell of claim 25, wherein the plant cell is selected from the group consisting of an apple cell, an *Arabidopsis* cell, a bajra cell, a banana cell, a barley cell, a bean cell, a beet cell, a blackgram cell, a chickpea cell, a chili cell, a cucumber cell, an eggplant cell, a favabean cell, a maize cell, a melon cell, a millet cell, a mungbean cell, an oat cell, an okra cell, a *Panicum* cell, a papaya cell, a peanut cell, a pea cell, a pepper cell, a pigeonpea cell, a pineapple cell, a *Phaseolus* cell, a potato cell, a pumpkin cell, a rice cell, a sorghum cell, a soybean cell, a squash cell, a sugarcane cell, a sugarbeet cell, a sunflower cell, a sweet potato cell, a tea cell, a tomato cell, a tobacco cell, a watermelon cell, and a wheat cell.

27. The multiple inducible gene modulation system of claim 4, wherein said nuclear receptor ligand binding domain is selected from the group consisting of a vertebrate retinoid X receptor ligand binding domain; an invertebrate retinoid X receptor ligand binding domain; an ultraspiracle protein ligand binding domain; and a chimeric ligand binding domain comprising two polypeptide fragments, wherein the first polypeptide fragment is from a vertebrate retinoid X receptor ligand binding domain, an invertebrate retinoid X receptor ligand binding domain, or an ultraspiracle protein ligand binding domain, and the second polypeptide fragment is from a different vertebrate retinoid X receptor ligand binding domain, invertebrate retinoid X receptor ligand binding domain, and an ultraspiracle protein ligand binding domain.

28. The multiple inducible gene modulation system of claim 4, wherein said ecdysone receptor ligand binding domain is selected from the group consisting of a Lepidopteran ecdysone receptor ligand binding domain, a Dipteran ecdysone receptor ligand binding domain, an Arthropod ecdysone receptor ligand binding domain, an Orthopteran ecdysone receptor ligand binding domain, a Homopteran ecdysone receptor ligand binding domain, a Hemipteran ecdysone receptor ligand binding domain, a spruce budworm *Choristoneura fumiferana* ecdysone receptor ligand binding domain, a yellow meal worm *Tenebrio molitor* ecdysone receptor ligand binding domain, a tobacco hornworm *Manduca sexta* ecdysone receptor ligand binding domain, a tobacco budworm *Heliothies virescens* ecdysone receptor ligand binding domain, a golmidge *Chironomus tentans* ecdysone receptor ligand binding domain, a silkworm *Bombyx mori* ecdysone receptor ligand binding domain, a squinting bush brown *Bicyclus anynana* ecdysone receptor ligand binding domain, a buckeye *Junonia coenia* ecdysone receptor ligand binding domain, a fruit fly *Drosophila melanogaster* ecdysone receptor ligand binding domain, a yellow fever mosquito *Aedes aegypti* ecdysone receptor ligand binding domain, a blowfly *Lucilia capitata* ecdysone receptor ligand binding domain, a sheep blowfly *Lucilia cuprina* ecdysone receptor ligand binding domain, a blowfly *Calliphora vicinia* ecdysone receptor ligand binding domain, a Mediterranean fruit fly *Ceratitis capitata* ecdysone receptor ligand binding domain, a locust *Locusta migratoria* ecdysone receptor ligand binding domain, an aphid *Myzus persicae* ecdysone receptor ligand binding domain, a fiddler crab *Celuca pugilator* ecdysone receptor ligand binding domain, an ixodid tick *Amblyomma americanum* ecdysone receptor ligand binding domain, and a white fly *Bamecia argentifoli* ecdysone receptor ligand binding domain.

29. The multiple inducible gene modulation system of claim 28, wherein said ecdysone receptor ligand binding domain is a spruce budworm *Choristoneura fumiferana* ecdysone receptor ligand binding domain.

30. The multiple inducible gene modulation system of claim 4, wherein said DNA binding domain is selected from the group consisting of a GAL4 DNA binding domain, a LexA DNA binding domain, a transcription factor DNA binding domain, a Group H nuclear receptor member DNA binding domain, a steroid/thyroid hormone nuclear receptor superfamily member DNA binding domain, a bacterial LacZ DNA binding domain, and an ecdysone receptor DNA binding domain.

31. The multiple inducible gene modulation system of claim 4, wherein said transactivation domain is selected from the group consisting of a Group H nuclear receptor member transactivation domain, a steroid/thyroid hormone nuclear receptor transactivation domain, a polyglutamine transactivation domain, a basic or acidic amino acid transactivation domain, a VP16 transactivation domain, a GAL4 transactivation domain, an NF-KB transactivation domain, a BP64 transactivation domain, a B42 acidic transactivation domain, and a p65 transactivation domain.

\* \* \* \* \*